(12) United States Patent
Smith

(10) Patent No.: US 10,898,134 B2
(45) Date of Patent: Jan. 26, 2021

(54) THERAPEUTIC CLOTHING HAVING RELEASABLY ATTACHED SENSORY STRIPS AND STRESS RELIEVING COMPONENTS INCORPORATED THEREIN

(71) Applicant: Renée Smith, Belvidere, NJ (US)

(72) Inventor: Renée Smith, Belvidere, NJ (US)

(*) Notice: Subject to any disclaimer, the term of this patent is extended or adjusted under 35 U.S.C. 154(b) by 16 days.

(21) Appl. No.: 15/882,166

(22) Filed: Jan. 29, 2018

(65) Prior Publication Data

US 2019/0059815 A1 Feb. 28, 2019

Related U.S. Application Data

(63) Continuation-in-part of application No. 15/686,748, filed on Aug. 25, 2017, now Pat. No. 10,589,058.

(51) Int. Cl.

| | |
|---|---|
| *A41D 1/00* | (2018.01) |
| *A41D 27/08* | (2006.01) |
| *A61B 5/00* | (2006.01) |
| *A61M 21/02* | (2006.01) |
| *A61M 21/00* | (2006.01) |
| *A41D 13/12* | (2006.01) |
| *A61B 5/16* | (2006.01) |

(52) U.S. Cl.
CPC .......... *A61B 5/6804* (2013.01); *A41D 1/005* (2013.01); *A41D 27/08* (2013.01); *A61B 5/4836* (2013.01); *A61M 21/02* (2013.01); *A41D 13/1236* (2013.01); *A41D 13/1254* (2013.01); *A41D 2400/32* (2013.01); *A61B 5/165* (2013.01); *A61B 5/6805* (2013.01); *A61M 2021/0022* (2013.01); *A61M 2021/0044* (2013.01); *A61M 2209/088* (2013.01)

(58) Field of Classification Search
CPC ..... A61M 21/02; A47G 9/02; A41D 13/1236; A41D 27/00; A41D 27/20; G02B 5/12
USPC ................. 2/243.1, 244, 255, 227, 228, 231
See application file for complete search history.

(56) References Cited

U.S. PATENT DOCUMENTS

| | | | | |
|---|---|---|---|---|
| 1,788,195 | A * | 1/1931 | Herman | A41D 1/086 2/227 |
| 5,569,345 | A * | 10/1996 | Kenyon | A41D 27/08 156/93 |
| 5,782,790 | A | 7/1998 | Allen | |

(Continued)

FOREIGN PATENT DOCUMENTS

WO        2012046068        4/2012

*Primary Examiner* — Katherine M Moran
(74) *Attorney, Agent, or Firm* — Doherty IP Law Group LLC

(57) ABSTRACT

Therapeutic clothing includes a garment adapted to be worn over a lower portion of a body having a waistband and first and second legs extending below the waistband. The therapeutic clothing has a first elongated sensory strip overlying an outside surface of the first leg and extending along the length of the first leg between the waistband and a lower end of the first leg, a first fastening system for releasably attaching the first elongated sensory strip to the outside surface of the first leg, a second elongated sensory strip overlying an outside surface of the second leg and extending along the length of the second leg between the waistband and a lower end of the second leg, and a second fastening system for releasably attaching the second elongated sensory strip to the outside surface of the second leg.

15 Claims, 32 Drawing Sheets

(56) References Cited

U.S. PATENT DOCUMENTS

| | | | | |
|---|---|---|---|---|
| 5,819,315 | A | * 10/1998 | Ruffa | A41D 13/0015 2/69 |
| 8,898,820 | B2 | 12/2014 | Sokolowski et al. | |
| 2006/0218692 | A1 | 10/2006 | Lamarque | |
| 2008/0222769 | A1 | 9/2008 | Natonson et al. | |
| 2009/0149698 | A1 | 6/2009 | Tastard | |
| 2013/0247277 | A1* | 9/2013 | Turbovich | A41B 13/005 2/243.1 |
| 2015/0064674 | A1* | 3/2015 | Turnbull | A63B 71/06 434/247 |
| 2015/0273178 | A1* | 10/2015 | Johnson | A61M 21/02 600/27 |
| 2015/0335853 | A1 | 11/2015 | Orewiler et al. | |
| 2016/0104389 | A1 | 4/2016 | Humphries | |
| 2016/0286877 | A1 | 10/2016 | Thierry | |
| 2017/0014595 | A1 | 1/2017 | Heath | |
| 2018/0000171 | A1 | 1/2018 | Pacheco | |
| 2018/0228224 | A1* | 8/2018 | Radcliffe | A61F 5/03 |
| 2019/0060604 | A1* | 2/2019 | Smith | A61M 21/02 |
| 2019/0116899 | A1* | 4/2019 | Williams | A41D 1/06 |

* cited by examiner

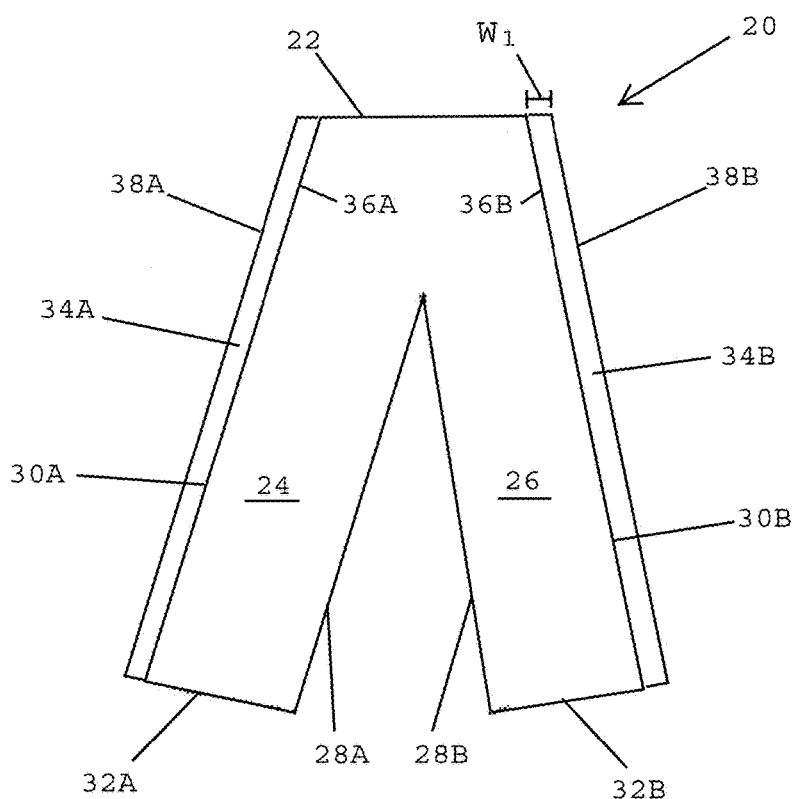
FIG. 1A
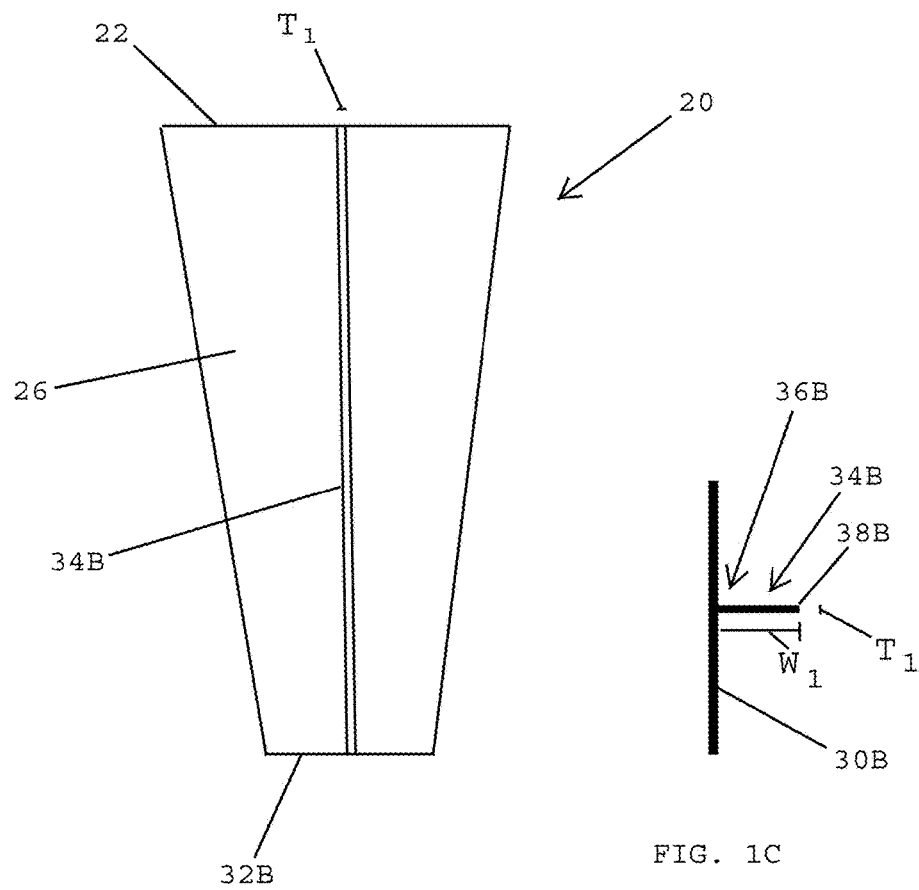
FIG. 1B
FIG. 1C

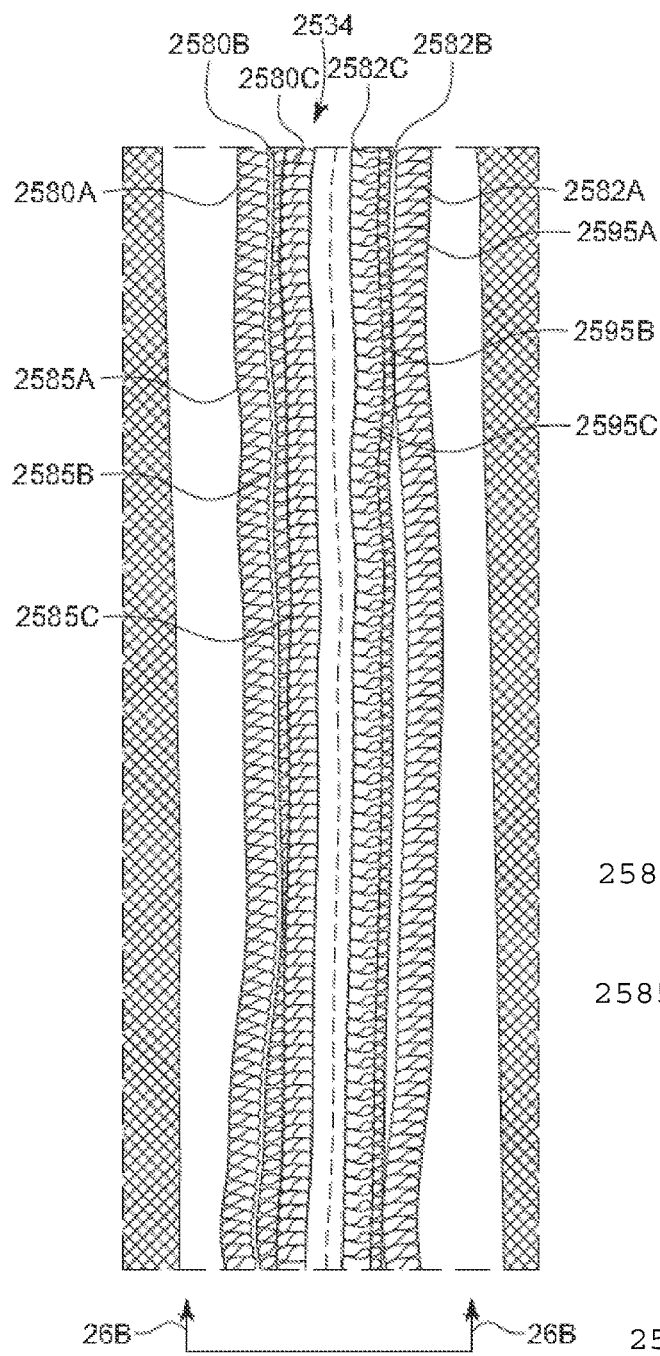
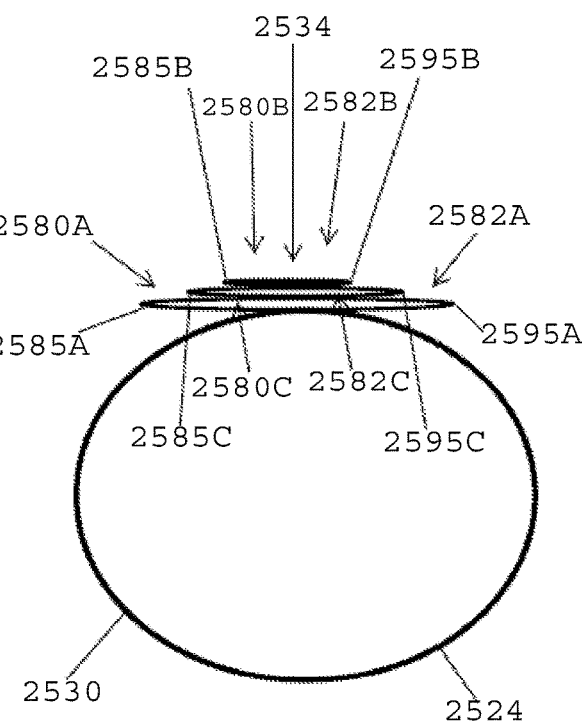
FIG. 26A
FIG. 26B

THERAPEUTIC CLOTHING HAVING RELEASABLY ATTACHED SENSORY STRIPS AND STRESS RELIEVING COMPONENTS INCORPORATED THEREIN

CROSS-REFERENCE TO RELATED APPLICATIONS

The present patent application is a continuation-in-part of U.S. patent application Ser. No. 15/686,748, filed Aug. 25, 2017, the disclosure of which is hereby incorporated by reference herein.

BACKGROUND OF THE INVENTION

Field of the Invention

The present patent application is generally related to clothing, and is more specifically related to therapeutic clothing having discrete sensory strips and stress relieving components incorporated therein.

Description of the Related Art

Autism is a neurological disorder characterized by symptoms including impaired social interaction, poor verbal and non-verbal communication skills, and restricted and repetitive behavior. It is believed that autism affects how information is processed in the brain by altering how nerve cells and their synapses connect and organize. The signs of autism usually appear within the first two years of a child's life.

Each person who lives with an autism spectrum disorder (ASD) is a unique case, unlike any other. Currently, societal awareness and understanding of ASD is not widespread. As parents, caregivers, teachers, and physicians learn more about autism, they are better able to identify and diagnose individuals displaying autism characteristics. In effort to provide the best quality of life, early detection and diagnosis of ASD is key.

Individuals diagnosed with ASD can benefit from multiple therapies and interventions. Early speech and/or behavioral interventions may help ASD children gain self-care, social, and communication skills. Unfortunately, many health insurance companies do not approve these therapies until a medical doctor or education team member conducts a detailed study and prepares a written report concluding that ASD is suspected. Next, many test appointments are required, which may take months to complete. After a full diagnosis has been made, the real journey begins including identifying an individual's specific needs and types of therapies that may be beneficial (e.g., speech therapy, occupational therapy, physical therapy, ABA therapy, music therapy).

Some ASD individuals cannot speak a word. Others may be able to utter a few words, and still others have various levels of discernable expressive language skills and receptive language abilities. Many ASD individuals have average to above-average intelligence. The language skill delay or complete inability of spoken language for the ASD person can mean a lifetime of frustration, which may be exhibited by actions that have been labeled as "negative behavior" patterns.

ASD individuals often have difficulty maintaining homeostasis within the nervous system, thereby inhibiting their ability to participate in effective learning and sometimes causing behaviors incongruent with social norms. Such identifiable behaviors may include constant movement, impulsivity, decreased attention span, inability to focus on a particular task and seeking of heavy-pressure related tasks.

At times, environmental stimuli may cause ASD individuals to feel overwhelmed and stressed. These negative feelings may be exaccerbated by the fact that an ASD individual is often unable to properly communicate the triggering source. Once an expression of discomfort is noticed, a caregiver or parent perceives the ASD person to be "acting-out." Unless the caregiver can identify the triggering source of the agitation, the ASD person's behavior can quickly escalate to more disruptive behavior including a public "meltdown." If the "meltdown" stage is reached, both the ASD individual and the caregiver are most likely experiencing heightened emotions. The ASD individual still feels the aggitation from overstimulation and is frustrated from the lack of an ability to express his or her needs and/or wants. The caregiver becomes frustrated because he or she does not understand what their loved one wants or needs.

Generally, the caregiver responds to the ASD individual by attempting to understand the cause of the melt-down and to calm the individual, while onlookers observe, stare and sometimes comment, which may cause the caregiver to become defensive towards the public and the ASD person to feel unaccepted, ashamed and/or embarrassed. Depending on the caregiver and his or her ability to communicate with the ASD individual, the caregiver may choose to gather the ASD individual and immediately exit the public setting. This may involve abandoning a shopping cart, leaving a meal on the table at a restaurant, leaving clothes at a laundromat, leaving a classmate's birthday party, leaving a family holiday, a playground, a public pool, etc.

Many ASD individuals find sensory input to effectuate calmness. In order to minimize negative behavior and "melt-downs," both the ASD individual and the caregiver seek to have the ASD individual's unique and favorite sensory input items on hand at all times. This can often be achieved by carrying the preferred sensory input items in a pocketbook, a backpack or a carry bag. Unfortunately, in many instances, at the exact time that a sensory input item is needed most, the ASD individual and/or a caregiver may realize that they have lost or left behind the preferred sensory input item.

There have been a number of efforts directed to ensuring that prefered sensory input items remain available for use at all times. For example, U.S. Patent Application Publication No. 2015/0273178 to Johnson discloses clothing having on-board fidgets and texture areas attached to the clothing in order to alleviate the symptoms of neurological dysfunction, reduce stress, and provide an avenue for relief and comfort for individuals who respond to sensory information differently. The on-board fidgets can include texture areas, chewing areas, vibrating inserts, weights, olfactory, auditory, and touch stimuli. The on-board fidgets are designed to be discrete so that individuals may use and enjoy them without feeling awkward or different. Some of the on-board fidgets may be removable and replaceable.

U.S. Patent Application Publication No. 2015/0335853 to Orewiler et al. discloses a weighted garment including a fabric shell having a quilted pattern in the form of a plurality of quilted squares. The weighted garment further includes a weighted filling housed and substantially evenly distributed within each of the plurality of quilted squares. The weighted garment applies deep pressure and tactile inputs for utilization of the proprioceptive and tactile systems to assist individuals with identified challenges of the nervous system and neurologically typical individuals with situational anxiety and related conditions.

In spite of the above advances, there remains a continuing need for therapeutic clothing having sensory tools incorporated therein.

SUMMARY OF THE INVENTION

In one embodiment, in order to provide ASD individuals with an avenue for relieving stress and anxiety, therapeutic clothing is provided that has sensory strips and/or sensory items (e.g., tassles) incorporated therein. In one embodiment, ASD individuals may utilize the sensory strips and/or sensory items during daily activities including travelling to and from school, engaging in classroom activities, on the playground, at home, during car rides, and at any time when "waiting" is required. The therapeutic clothing disclosed herein preferably provides ASD individuals with independent control and use of the therapeutic clothing and the attached sensory items at all times. Because the sensory strips and sensory items are attached to the clothing (e.g., sewn to the clothing), during stressful events there is no requirement to locate a preferred sensory item and no chance that the preferred sensory item was left behind because the preferred sensory item remains attached to or part of the clothing at all times.

In one embodiment, when pants or shorts are provided with sensory strips, the ASD individual tends to maintain his or her hands at the sides. When walking, the ASD individual tends to swipe his or her hands over the sensory strips as the arms move to the front and the rear, which also results in the hands staying at the sides. The cumulative effect is that the hands are maintained at the sides and negative actions such as pulling hair, pulling lips, grabbing nearby objects are minimized.

In one embodiment, therapeutic clothing preferably includes a garment having a waistband and first and second legs extending below the waistband. In one embodiment, the garment includes a first sensory strip attached to an outside surface of the first leg and extending between the waistband and a lower end of the first leg. In one embodiment, the first sensory strip has an inner edge attached to the outside surface of the first leg and a free outer edge that is spaced from the inner edge of the first sensory strip. In one embodiment, the garment includes a second sensory strip attached to an outside surface of the second leg and extending between the waistband and a lower end of the second leg. In one embodiment, the second sensory strip has an inner edge attached to the outside surface of the second leg and a free outer edge that is spaced from the inner edge of the second sensory strip.

In one embodiment, the first and second sensory strips are elongated. In one embodiment, the first and second sensory strips have widths that project away from one another on opposite sides of the garment.

In one embodiment, each of the first and second sensory strips has a length of about 5-40 inches, a width of about 0.5-3 inches, and a thickness of about 0.0625-0.25 inches. In one embodiment, each of the first and second sensory strips has a width of about 1 inch.

In one embodiment, the free outer edge of the first sensory strip includes first cross-stitching that defines a first thicker section of the first sensory strip, and the free outer edge of the second sensory strip includes second cross-stitching that defines a second thicker section of the second sensory strip.

In one embodiment, the first and second sensory strips may be made of various materials including but not limited to cotton, cellulose, polymers, spandex, silicon, tweed, nylon, silk, satin, corduroy, polyester, rayon, velvet, nylon, cashmere, fur, fake fur, fleece, and combinations thereof.

In one embodiment, the first sensory strip includes a first stiffening element embedded therein that extends along a length of the first sensory strip, and the second sensory strip includes a second stiffening element embedded therein that extends along a length of the second sensory strip.

In one embodiment, the free outer edge of the first sensory strip preferably has a first roughened element having the appearance and/or the look and feel of zipper teeth that extend along a length of the first sensory strip, and the free outer edge of the second sensory strip preferably has second roughened element having the appearance and/or the look and feel of zipper teeth that extend along a length of the second sensory strip.

In one embodiment, the first sensory strip may have a first supplemental sensory strip that projects from a front face of the first sensory strip and a second supplemental sensory strip that projects from a rear face of the first sensory strip and away from the first supplemental sensory strip.

In one embodiment, the second sensory strip may have a first supplemental sensory strip that projects from a front face of the second sensory strip and a second supplemental sensory strip that projects from a rear face of the second sensory strip and away from the first supplemental sensory strip of the second sensory strip.

In one embodiment, the garment having sensory strips and/or stress relieving components incorporated therein may be pants, trousers, sweat pants, warm-up pants, shorts, athletic shorts, pajamas, bathing suits, swimming trunks, vests, jackets, scarves, wraps, and/or blankets.

In one embodiment, the therapeutic clothing may include a second garment that covers an upper portion of a body, and a third sensory strip attached to a surface of the second garment, whereby the third sensory strip has an inner edge attached to the surface of the second garment and a free outer edge that is spaced from the inner edge of the third sensory strip.

In one embodiment, the second garment includes a shirt having two arms and a central torso section. In one embodiment, the inner edge of the third sensory strip is attached to one of the arms of the shirt. In one embodiment, the inner edge of the third sensory strip is attached to a lower end of the central torso section.

In one embodiment, therapeutic clothing preferably includes a garment adapted to be worn over a lower portion of a body having a waistband and first and second legs extending below the waistband.

In one embodiment, the garment may include a first elongated sensory strip attached to an outside surface of the first leg and extending along the length of the first leg between the waistband and a lower end of the first leg, whereby the first elongated sensory strip has an inner edge attached to the outside surface of the first leg and a free outer edge that is spaced from the inner edge of the first sensory strip.

In one embodiment, the garment may include a second elongated sensory strip attached to an outside surface of the second leg and extending along the length of the second leg between the waistband and a lower end of the second leg, whereby the second sensory strip has an inner edge attached to the outside surface of the second leg and a free outer edge that is spaced from the inner edge of the second sensory strip.

In one embodiment, a clothing item may have a sensory strip releasably attached to the clothing item, which enables an individual to selectively attached and detach the sensory strip from the clothing item. In one embodiment, the clothing item and/or the sensory strip includes attachment structures incorporated therein including hook and loop fastener strips (i.e., VELCRO strips), zippers, zipper teeth, buttons, snaps and magnets.

As used herein, the terminology "releasably attached" means an attachment that is not a permanent attachment (e.g., attached via a sewn thread). A releasable attachment enables two items to be repeatedly and selectively attached and detached from one another without damaging or destroying the structure that forms the attachment. Hook and loop fastener strips are an example of a structure that allows two items to be releasably attached because the strips may be repeatedly pressed together for forming a temporary attachment and then pulled apart to separate the two strips from one another.

In one embodiment, a first part of a hook and loop fastener strip is provided on an outside surface of a clothing item and a second part of a hook and loop fastener strip is provided on a sensory strip. The hook and loop fastener strips can be pressed together for releasably attaching the sensory strip to the clothing item. The sensory strip will remain releasably attached to the clothing item as long as the hook and loop fastener strips engage one another.

In one embodiment, an accessory kit may include two or more sensory strips, each sensory strip having a hook and loop fastener strip. Each sensory strip may have a unique color, pattern, fabric, texture, stitching, etc., whereby a user may customize an article of clothing by selecting which sensory strip to attach to clothing. In one embodiment, a user may have a favorite sensory strip that may be releasably attached to whatever clothing item the user happens to be wearing. As a result, a single sensory strip may be releasably secured to different clothing items. In one embodiment, different sensory strips may be releasably secured in an interchangeable manner to the same location on a single clothing item.

In one embodiment, a releasably attachment may be formed using a zipper. In one embodiment, a first part of a zipper strip having teeth is provided on an outside surface of a clothing item (e.g., the leg of pants) and a second part of a zipper strip having teeth is provided on a sensory strip. The zipper strips may be meshed together using a slider for releasbly attaching the sensory strip to the clothing item. The zipper may be opened for detaching the sensory strip from the clothing. In one embodiments, magnets, snaps and buttons may be used in a similar manner for releasably attaching sensory strips to clothing items.

In one embodiment, therapeutic clothing includes a garment with a waistband and first and second legs extending below the waistband, a sensory strip overlying an outside surface of the first leg and extending between the waistband and a lower end of the first leg, and a fastening system for releasably attaching the sensory strip over the outside surface of the first leg.

In one embodiment, the therapeutic clothing may include a second sensory strip overlying an outside surface of the second leg and extending between the waistband and a lower end of the second leg, and a second fastening system for releasably attaching the second sensory strip over the outside surface of the second leg.

In one embodiment, the first fastening system includes first hook and loop strips attached to the sensory strip and the outside surface of the first leg, and the second fastening system includes second hook and loop strips attached to the second sensory strip and the outside surface of the second leg.

In one embodiment, the first fastening system includes a first zipper with a first zipper half attached to the first sensory strip and a second zipper half attached to the outside surfaced of the first leg. In one embodiment, the first sensory strip is releasably attached to the first leg when the first zipper is closed and the first sensory strip is detached from the first leg when the zipper is opened.

In one embodiment, the second fastening system includes a second zipper with a first zipper half attached to the second sensory strip and a second zipper half attached to the outside surfaced of the second leg. In one embodiment, the second sensory strip is releasably attached to the second leg when the second zipper is closed and the second sensory strip is detached from the second leg when the second zipper is opened.

In one embodiment, the first fastening system may include hook and loop fastener strips, zippers, zipper teeth, buttons, snaps, magnets and/or laces.

In one embodiment, therapeutic clothing preferably includes a garment adapted to be worn over a lower portion of a body including a waistband and first and second legs extending below the waistband, a first elongated sensory strip overlying an outside surface of the first leg and extending along a length of the first leg between the waistband and a lower end of the first leg, a first fastening system for releasably attaching the first elongated sensory strip to the outside surface of the first leg, a second elongated sensory strip overlying an outside surface of the second leg and extending along a length of the second leg between the waistband and a lower end of the second leg, and a second fastening system for releasably attaching the second elongated sensory strip to the outside surface of the second leg.

In one embodiment, the first and second sensory strips project away from one another on opposite sides of the garment, have a length of about 5-40 inches, a width of about 1 inch, and a thickness of about 0.0625-0.25 inches.

In one embodiment, the first sensory strip has a first free outer edge with first cross-stitching that defines a first thicker section of the first sensory strip, and the second sensory strip has a second free outer edge with second cross-stitching that defines a second thicker section of the second sensory strip.

In one embodiment, the first sensory strip includes a first stiffening element embedded therein that extends along a length of the first sensory strip, and the second sensory strip includes a second stiffening element embedded therein that extends along a length of the second sensory strip.

In one embodiment, therapeutic clothing includes a garment having a waistband and first and second legs extending below the waistband, a plurality of sensory strips adapted to overlie an outside surface of the first leg, whereby each of the sensory strips has unique properties associated therewith, and a fastening system provided at the outside surface of the first leg for releasably attaching the sensory strips over the outside surface of the first leg. In one embodiment, the sensory strips are interchangeable and are adapted to be releasably attached one at a time over the outside surface of the first leg.

These and other preferred embodiments of the present invention will be described in more detail below.

BRIEF DESCRIPTION OF THE DRAWINGS

FIG. 1A shows pants having sensory strips attached to the outsides of the legs, in accordance with one embodiment of the present patent application.

FIG. 1B shows a right side view of the pants shown in FIG. 1A.

FIG. 1C shows a cross-sectional view of the pants shown in FIG. 1A taken along line 1C-1C of FIG. 1A.

FIG. 26A shows a top plan view of a sensory strip assembly, in accordance with one embodiment of the present patent application.

FIG. 26B shows a cross-sectional view of the sensory strip assembly of FIG. 26A.

DETAILED DESCRIPTION OF PREFERRED EMBODIMENTS

Figure 2A:
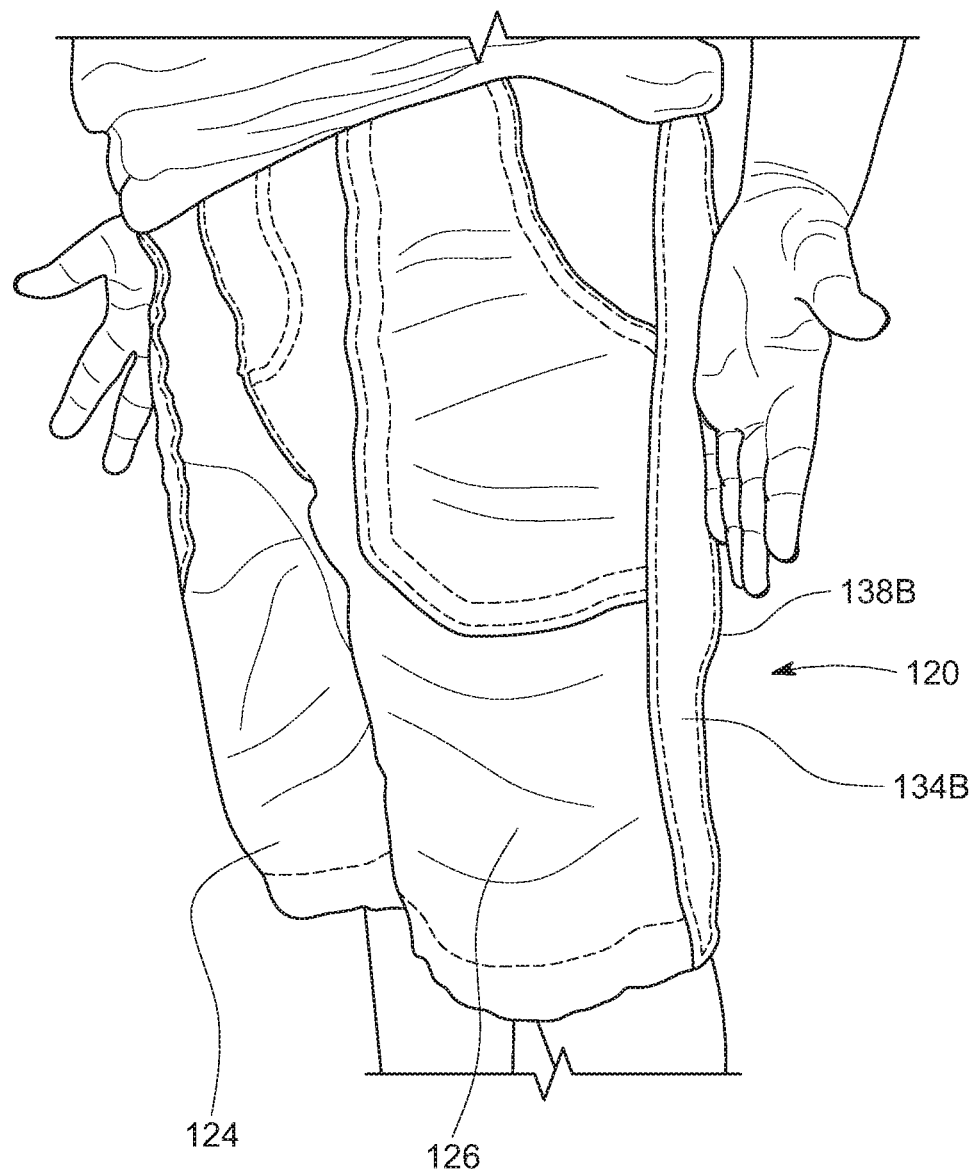
FIG. 2A shows a perspective view of shorts having sensory strips extending from the outsides of the legs, in accordance with one embodiment of the present patent application.

Referring to FIG. 1A, in one embodiment, pants 20 have a waistband 22 located at an upper end and first and second legs 24, 26 that extend down from the waistband 22. The first leg 24 has an inside surface 28A, and an outside surface 30A that extends from the waistband 22 to the lower end 32A of the first leg 24. A first sensory strip 34A is secured to the outer edge 30A of the first leg 24. In one embodiment, the first sensory strip 34A extends from the waistband 22 to the lower end 32A of the first leg 24. In one embodiment, the first sensory strip 34A may extend only part of the way between the waistband 22 and the lower end 32A of the first leg 24. In one embodiment, the first sensory strip 34A has an inner edge 36A that is sewn to the outside surface 30A of the first leg 24, and an outer edge 38A that is free to move. Thus, the first sensory strip 34A is a flap of material that extends outwardly from the outside surface 30A of the first leg 24. In one embodiment, the first sensory strip 34A has a width that is greater than the thickness of the first sensory strip. In one embodiment, the first sensory strip 34A has a width $W_1$ of about one-three inches, and more preferably about one inch. In one embodiment, the first sensory strip 34A has a thickness $T_1$ (FIG. 1B) of about 1/16-1/4 inches and more preferably about 1/8$^{th}$ of an inch.

In one embodiment, the pants 20 desirably include a second sensory strip 34B that is attached to an outside surface 30B of the second leg 26, which faces away from an inside surface 28B of the second leg. In one embodiment, the second sensory strip 34B extends between the waistband 22 and the lower end 32B of the second leg 26. In one embodiment, the second sensory strip 34B extends only part of the way between the waistband 22 and the lower end 32B of the second leg 26. In one embodiment, the second sensory strip 34B preferably has an inner edge 36B that is sewn to the outside surface 30B of the second leg 26 and a second free edge 38B that extends between the waistband 22 and the lower end 32B of the second leg 26. Because the second sensory strip 34B is attached to the second leg 26 along only one edge, the free edge 38B of the second sensory strip defines a flap of material that is able to move freely relative to the outside surface 30B of the second leg 26. In one embodiment, the second sensory strip 34B has a width and a thickness that is similar to the dimensions for the first sensory strip described above.

FIG. 1C shows the second sensory strip 34B sewn to the outside surface 30B of the second leg 26 of the pants 20 (FIG. 1A). The second sensory strip 34B has an inner edge 36B that is sewn to the outside surface 30B of the second leg 26 and a free outer edge 38B that is not sewn to the pants and that is free to move. In one embodiment, the free outer edge 38B defines a flap of material that may be engaged by the hands and fingers of an individual. The second sensory strip 34B has a width $W_1$ that is greater than the thickness T1. In one embodiment, the width W1 is about 0.5-3 inches and more preferably about one inch and the thickness $T_1$ is about 1/8$^{th}$ inch.

In one embodiment, when wearing the pants shown in FIGS. 1A-1C, an individual may use his or her hands and fingers to engage the free outer edges 38A, 38B of the first and second sensory strips 34A, 34B to provide sensory feedback, which has a calming effect on the individual. In one embodiment, each of the free outer edges 38A, 38B may be rubbed between a forefinger and a thumb to provide sensory feedback and a calming effect for the individual. The sensory strips 34A, 34B desirably provide a place for an individual's hands to go, and may tend to keep the individual's hands at his or her sides when walking. Because the hands are occupied when engaging the sensory strips, the individual is less likely to engage in undesirable activities such as pulling hair, pulling on a lip, etc.

Figure 2B:
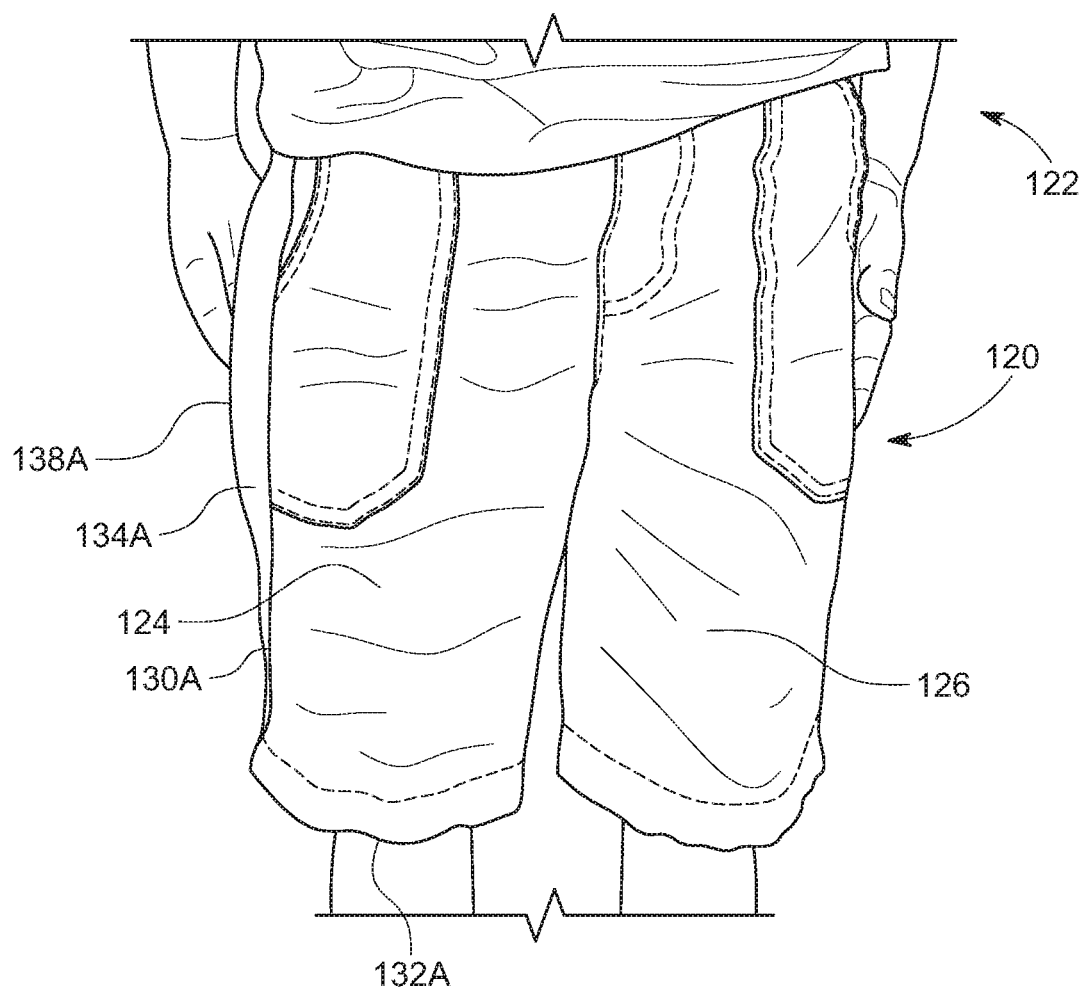
FIG. 2B shows another perspective view of the shorts shown in FIG. 2A.

Referring to FIG. 2A, in one embodiment, shorts 120 may include a first leg 124 and a second leg 126. In one embodiment, the first and second sensory strips are preferably sewn to the outside surfaces of each of the first and second legs 124, 126. FIG. 2B shows a second sensory strip 134B sewn to the outside surface of the second leg 126. The second sensory strip 134B has a free outer edge 138B that may be engaged by the hands and/or fingers of an individual to provide sensory feedback and a calming, soothing effect. The free outer edge 138 provides a flap of material that extends along the outside of the second leg 126, which may be engaged by the individual's hands and/or fingers.

FIG. 2B shows a first sensory strip 134A secured to the outside surface 130A of the first leg 124 of the shorts 120. The first sensory strip 134A preferably extends from the waistband region 122 to the lower end 132A of the first leg 124. The first sensory strip 134A has a free outer edge 138A that may be engaged by an individual's hands and/or fingers to provide a calming, soothing effect, and/or a place for the individual's hands and fingers to go. In one embodiment, the sensory strips may extend only part of the way between the waistband 122 and the lower ends of the respective legs 124, 126.

Figure 2C:
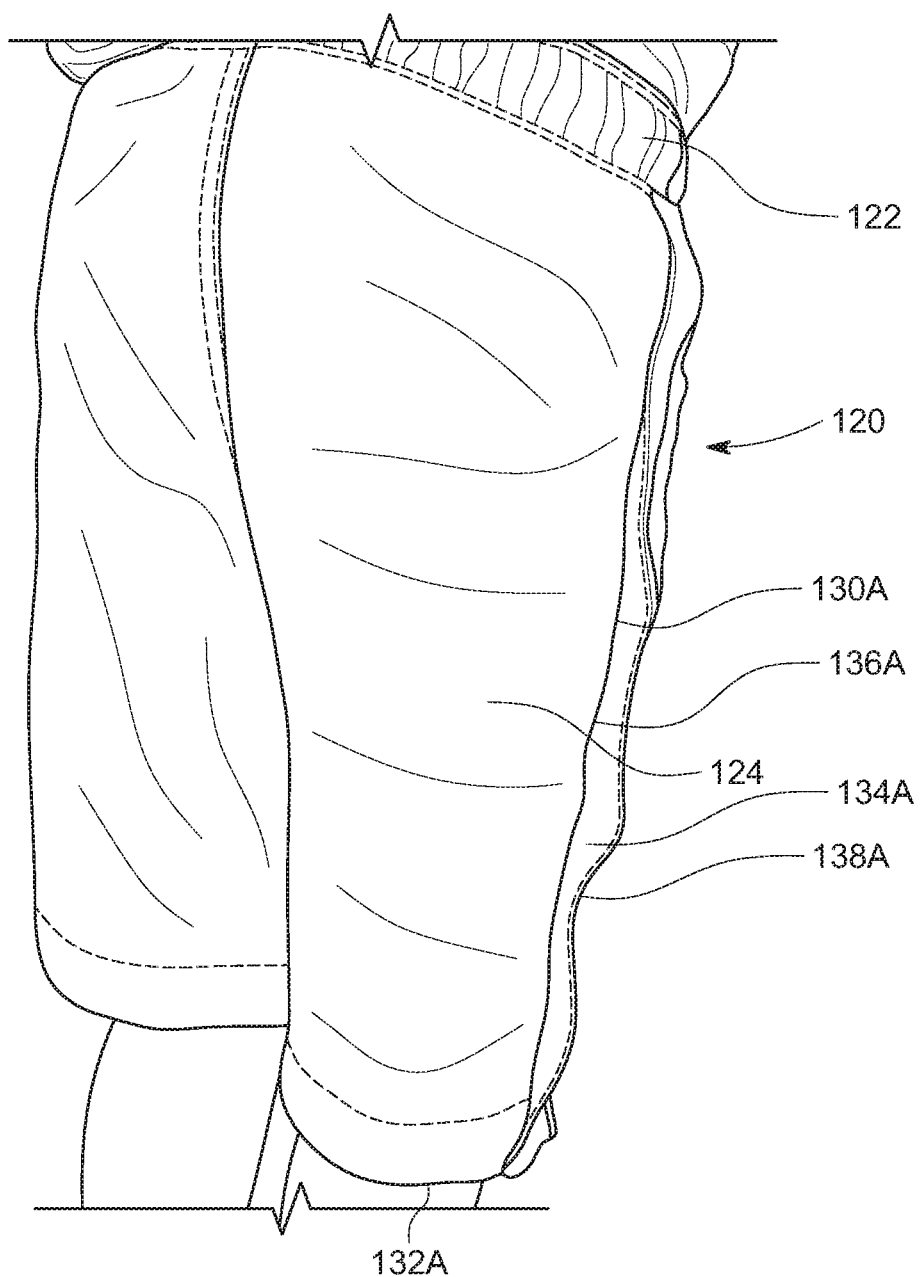
FIG. 2C shows a rear view of the shorts shown in FIGS. 2A and 2B.

Referring to FIG. 2C, in one embodiment, the first sensory strip 134A extends from the waistband 122 to the lower end 132 of the first leg 124 of the shorts 120. The first sensory strip 134 has an inner edge 136A that is sewn to an outside surface 130A of the first leg 124 and a free outer edge 138A that may be engaged by an individual's hands and/or fingers. The first sensory strip 134A provides a flap of material that extends between the waistband 126 and the lower end 132A of the first leg 124. In one embodiment, the free outer edge 138A of the flap of material may be engaged by a user by pinching the free edge 138A between a forefinger and thumb to provide a calming, soothing effect.

Figure 3A:
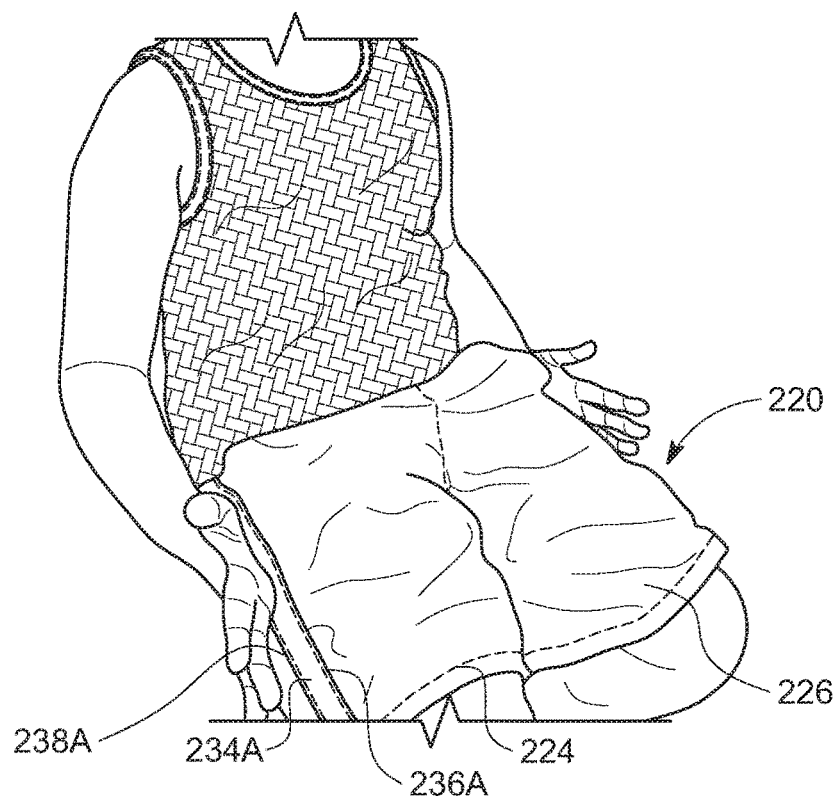
FIG. 3A shows an individual wearing shorts having sensory strips attached to the outsides of the legs, in accordance with one embodiment of the present patent application.

Referring to FIG. 3A, in one embodiment, shorts 220 have a first leg 224 and a second leg 226. The shorts 220 may have first and second sensory strips secured to the outside surfaces of the respective first and second legs 224, 226. In one embodiment, the first and second sensory strips are sewn to the first and second legs 224, 226. In one embodiment, the first sensory strip 234A has an inner edge 236A that is sewn to the outside surface of the first leg 224, and a free outer edge 238A that provides a readily accessible edge that may be engaged an individual's hands and/or fingers.

Figure 3B:
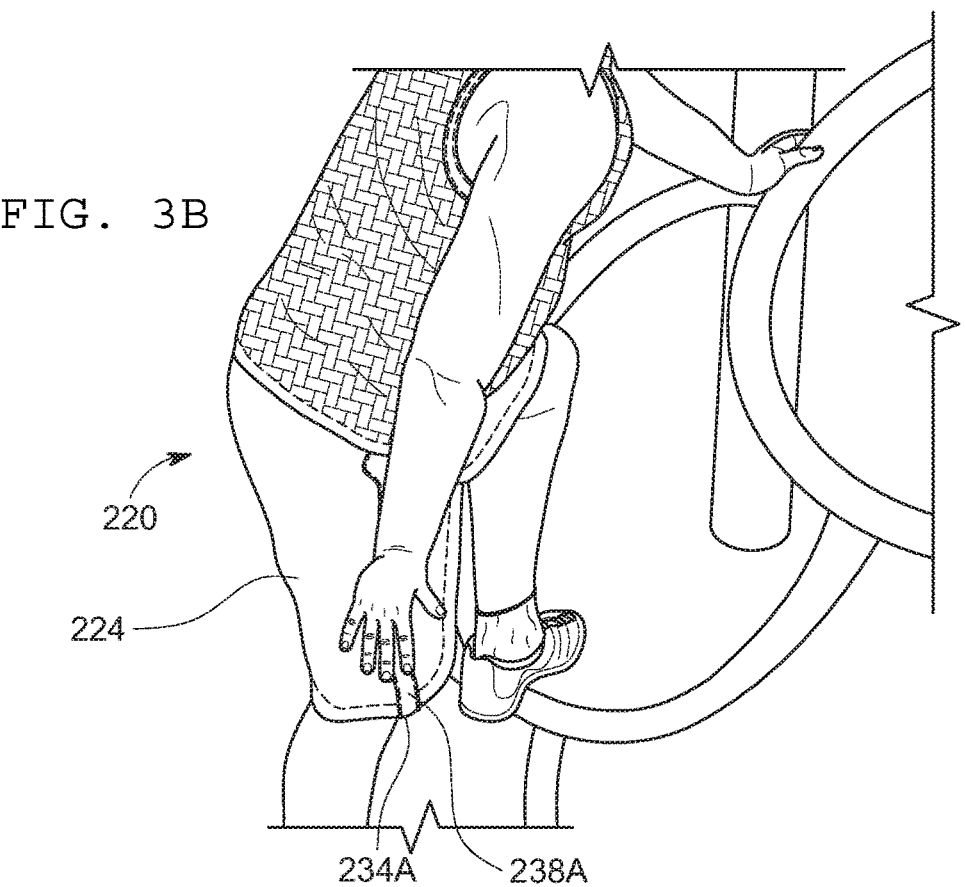
FIG. 3B shows the individual of FIG. 3A using his hand to touch one of the sensory strips.

Referring to FIG. 3B, in one embodiment, when the shorts 220 are worn by an individual, the individual may engage the free outer edge 238A of the first sensory strip 234A with his fingers to provide a sensory feedback and a calming, soothing effect. Because the first sensory strip 234A is permanently attached to the shorts 220, there is no need for the individual to search for or carry a sensory input item in a hand. The first sensory strip 234A is always accessible to the individual wearing the shorts because the first sensory strip 234A is permanently sewn to the first leg 224 of the shorts 220.

Figure 4A:
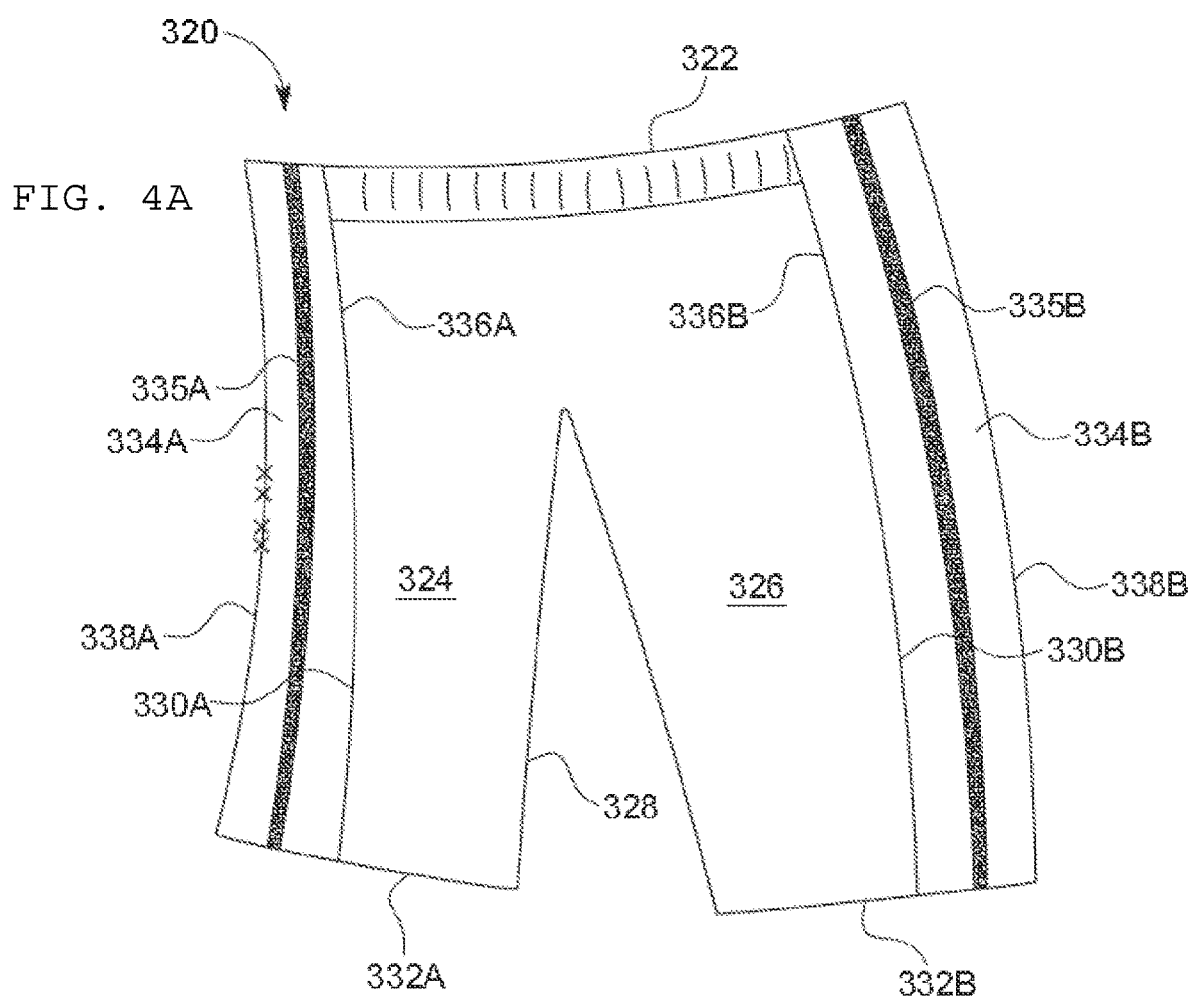
FIG. 4A shows shorts having first and second legs with sensory strips attached to the outsides of the legs, in accordance with embodiment of the present patent application.

Referring to FIG. 4A, in one embodiment, shorts 320 have a waistband 322 and first and second legs 324, 326 that extend down from the waistband 322. In one embodiment, the first leg 324 has an inside surface 328A, and an outside surface 330A that extends between the waistband 322 and the lower end 332 of the first leg 324. The shorts 320 have a first sensory strip 334A sewn to the outside surface 330A of the first leg 324. The first sensory strip 334A preferably extends between the waistband 322 and a lower end 332 of the first leg 324. The first sensory strip 334A preferably has an inner edge 336A that is sewn to the outside surface 330A and a free outer edge 338A. The first sensory strip 334A provides a flap of material with a free outer edge 338A that extends between the waistband 322 and a lower 332 of the first leg 324. The free outer edge 338A may be engaged by an individual's hands and/or fingers to provide sensory feedback and a calming, soothing effect.

In one embodiment, the first sensory strip 334A has supplemental sensory strips that project from the front and rear faces of the first sensory strip. In FIG. 4A, a first supplemental sensory strip 335A projects from a front face of the first sensory strip 334A, and a second supplemental sensory strip (not shown) projects from a rear face of the first sensory strip 334A.

In one embodiment, the second leg 326 has a second sensory strip 334B sewn to an outside surface 330B of the second leg. The second sensory strip 334B has an inner edge 336B sewn to the outside surface of the second leg 326 and a free outer edge 338B that is free to move and is engageable by an individual's hands and/or fingers. In one embodiment, the second sensory strip 334B preferably includes a pair of supplemental sensory strips that project from the respective front and rear faces of the second sensory strip. FIG. 4A shows a first supplemental sensory strip 335B projecting from the front face of the second sensory strip 334B. The second sensory strip 334B desirably includes a second supplemental sensory strip the projects from a rear face thereof (not shown in FIG. 4A).

Figure 4B:
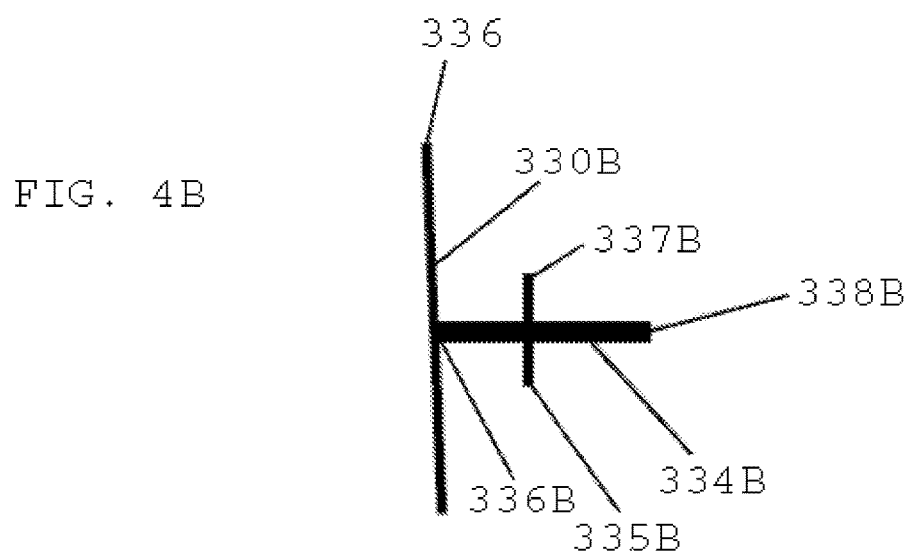
FIG. 4B shows a cross-sectional view of a sensory strip attached to the outside of a leg taken along line 4B-4B of FIG. 4A, in accordance with one embodiment of the present patent application.

Referring to FIG. 4B, in one embodiment, the second sensory strip 334B is secured to the outside surface 330B of the second leg 326. In one embodiment, the inner edge 336B of the second sensory strip 334B is sewn to the outside surface 330B of the second leg 326. The second sensory strip 334B preferably has a free outer edge 338B that may be engaged by an individual. The second sensory strip 338B desirably includes a first supplemental sensory strip 335B that projects to the front face of the second sensory strip 334B, and a second supplement sensory strip 337B that projects to the rear face of the second sensory strip 334B. In one embodiment, the structure of the second sensory strip 334B provides three free edges for an individual to engage. In one embodiment, the free edges include the free edge 338B of the second sensory strip 334B, and the two free outer edges of the supplemental sensory strips 335B and 337B. In one embodiment, the second sensory strip 334B is preferably wider than the supplemental sensory strips 335B, 337B.

Figure 5:
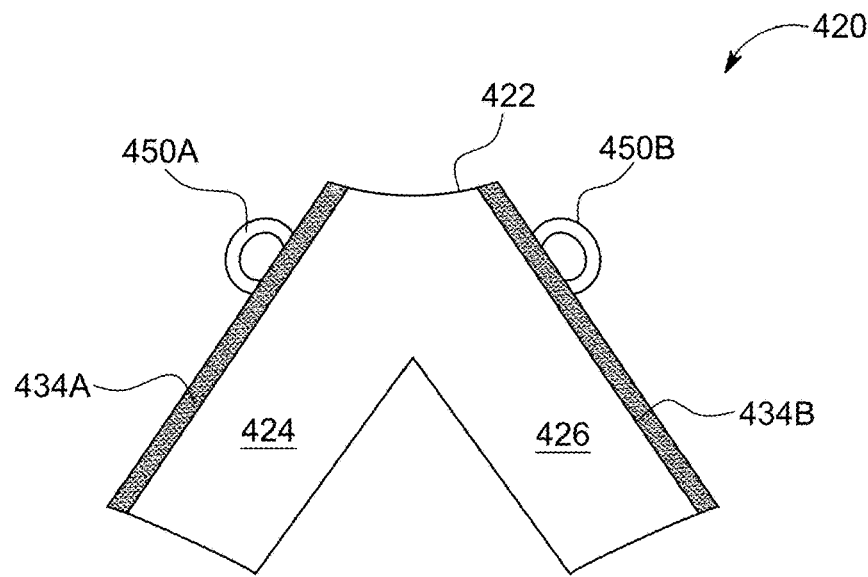
FIG. 5 shows pants having first and second legs with sensory strips and carpenter's loops attached to the outsides of the first and second legs, in accordance with one embodiment of the present patent application.

Referring to FIG. 5, in one embodiment, pants 420 have a waistband 422 and first and second legs 424, 426. A first sensory strip 434A is sewn to the outside of the first leg 424 and a second sensory strip 434B is sewn to the outside of the second leg 426. The first and second sensory strips 434B, 434B are sewn to the outsides of the respective first and second legs 424, 426 as described above to provide sensory strips having free outer edges that may be engaged by an individual's hands and/or fingers for providing sensory feedback and a calming, soothing effect. In one embodiment, the sensory strips may be attached to other garments including the legs of shorts, a skirt or a dress.

In one embodiment, a first carpenter's loop 450A is sewn to the outside of the first leg 424 and a second carpenter's loop 450B is sewn to the outside of the second leg 426. In one embodiment, the first and second carpenter's loops 450A, 450B may be sewn to the free edges of the respective first and second sensory strips 434A, 434B.

Figure 6:
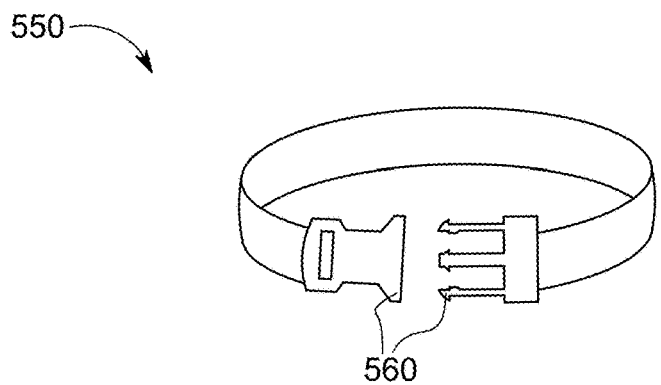
FIG. 6 shows a sensory attachment for clothing, in accordance with one embodiment of the present patent application.

Referring to FIG. 6, in one embodiment, a sensory loop attachment 550 may have a clasp 560 that enables the sensory loop attachment 550 to be attached to and/or decoupled from clothing. In one embodiment, the sensory loop attachment may be secured to a carpenter's loop 450A, 450B (FIG. 5). In one embodiment, the sensory loop attachment 550 may be made of various materials that provide a calming, soothing effect such as spandex, silicon, tweed, nylon, satin, polyester, cotton, rayon, velvet, nylon, cashmere, fur and/or fake fur. In one embodiment, a sensory strip (e.g., strip 34A in FIG. 1A) may be attached to the sensory loop attachment.

Figure 7:
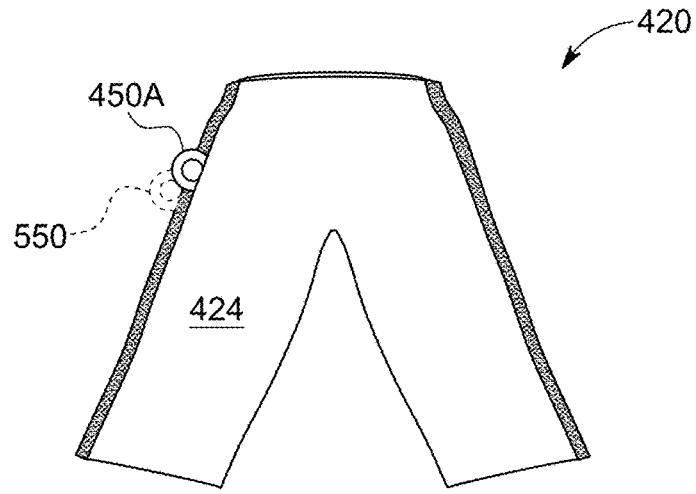
FIG. 7 shows the sensory attachment of FIG. 6 secured to a carpenter's loop, in accordance with embodiment of the present patent application.

Referring to FIG. 7, in one embodiment, the sensory loop attachment 550 may be secured to a carpenter's loop 450A attached to a leg 424 of pants 420. In one embodiment, different sensory loop attachments may be secured to pants, whereby each sensory loop attachment has different materials and/or soothing properties.

Figure 8:
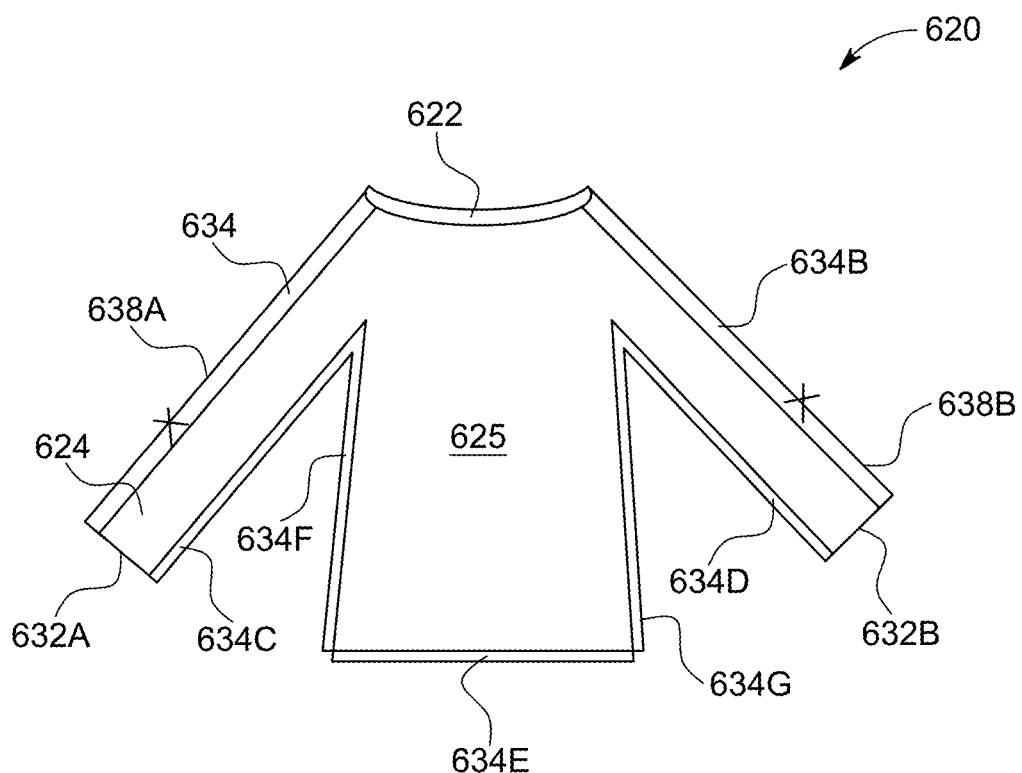
FIG. 8 shows a shirt having sensory strips attached thereto, in accordance with one embodiment of the present patent application.

Referring to FIG. 8, in one embodiment, a shirt 620 includes a neck 622, a first arm 624, a second arm 626, and a central torso section 625 that covers a torso of an individual who is wearing the shirt. In one embodiment, a first sensory strip 634A is sewn to the outside of the first arm 624. The first sensory strip 634A preferably extends from the neck opening 622 to the lower end 632A of the first arm 624. The first sensory strip 634A is secured to the first arm 624 as described above so that it has a free outer edge 638A that may be engaged by an individual wearing the shirt 620.

The shirt 620 preferably includes a second sensory strip 634B that is sewn to the outside of the second arm 626. The second sensory strip 634B preferably has a free outer edge 638B that may be engaged by an individual wearing the shirt. The second sensory strip 634B preferably extends from the neck 622 to a lower end 632B of the second arm 626.

In one embodiment, a third sensory strip 634C is sewn to the inside surface of the first arm 624. The third sensory strip 634C preferably extends from the armpit to the lower end 632A of the first arm 624.

In one embodiment, a fourth sensory strip 634D is sewn to the inside surface of the second arm 626. The fourth sensory strip 634D preferably extends from the armpit to the lower end 632B of the second arm 626.

In one embodiment, a fifth sensory strip 634E is sewn to the bottom of the central torso section 625, a sixth sensory strip 634F is sewn to a first side of the central torso section 625, a seventh sensory strip 634G is sewn to the bottom of the central torso section 625.

Figure 9:
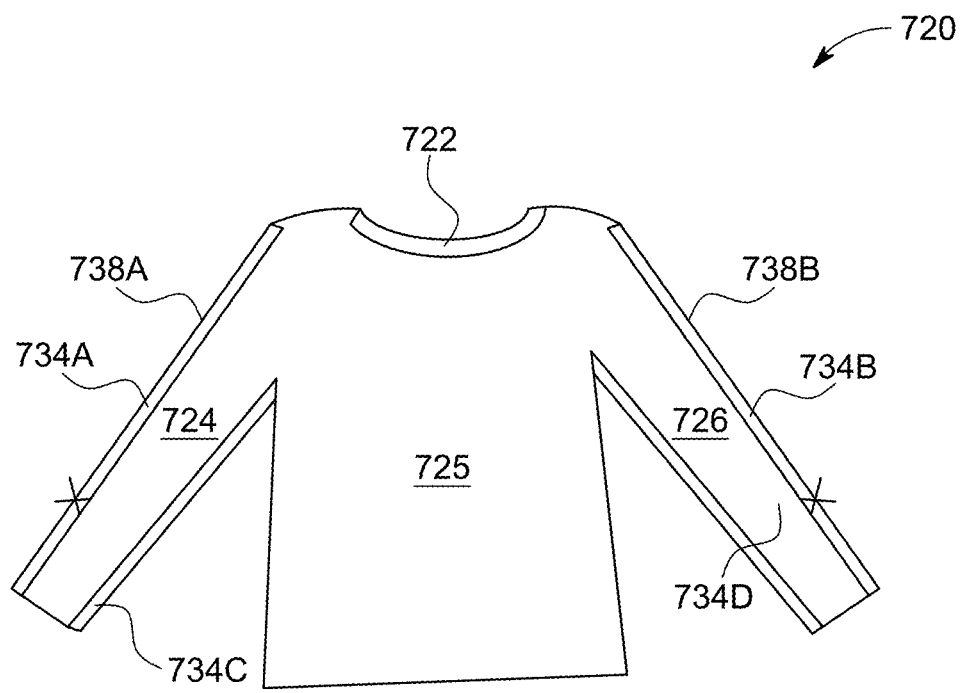
FIG. 9 shows a shirt having sensory strips attached thereto, in accordance with one embodiment of the present patent application.

Referring to FIG. 9, in one embodiment, a shirt 720 includes a neck 722, a first arm 724, a second arm 726, and a central torso section 725 that covers a torso of an individual wearing the shirt. In one embodiment, a first sensory strip 734A is sewn to the outside of the first arm 724. The first sensory strip 734A preferably extends from the neck opening 722 to the lower end 732A of the first arm 724. The first sensory strip 734A is secured to the first arm 724 as described above so that it has a free outer edge 738A that may be engaged by an individual wearing the shirt 720. In one embodiment, the free outer edge 738A may have additional stitching provided at the outer edge so that the outer edge is stiffer, more rugged, and/or provides enhanced tactile feedback for an individual engaging the outer edge with his/her hands and/or fingers.

The shirt 720 preferably includes a second sensory strip 734B that is sewn to the outside surface of the second arm 726. The second sensory strip 734B preferably has a free outer edge 738B that may be engaged by an individual wearing the shirt. The second sensory strip 734B preferably extends from the neck 722 to a lower end 732B of the second arm 726.

In one embodiment, the shirt 720 desirably has a third sensory strip 734C that is sewn to the inside surface of the first arm 724, which preferably extends from the armpit to the lower end 732A of the first arm 724. In one embodiment, the shirt 720 preferably has a fourth sensory strip 734D is sewn to the inside surface of the second arm 726, which preferably extends from the armpit to the lower end 732B of the second arm 726.

Figure 10:
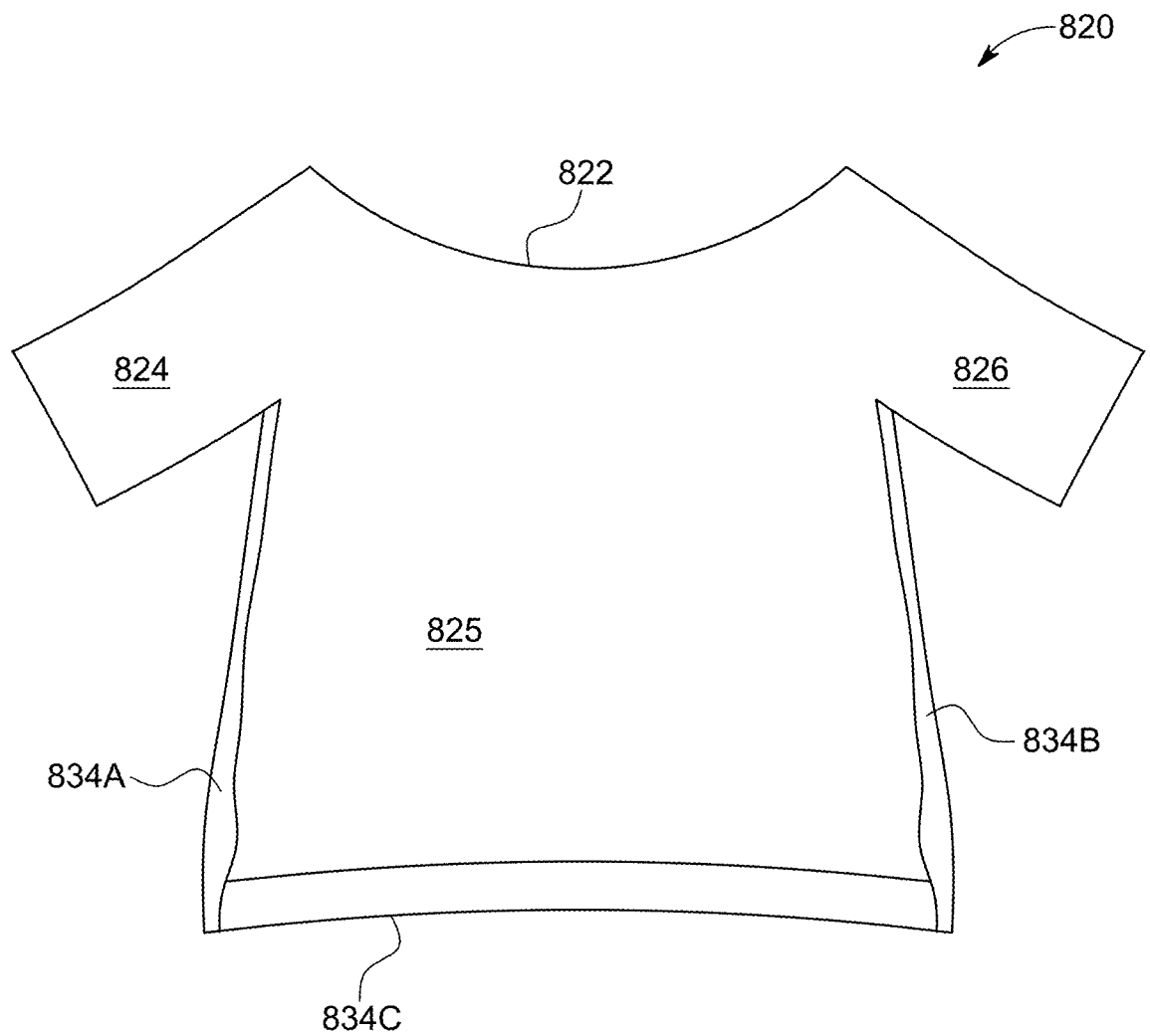
FIG. 10 shows a shirt having sensory strips attached thereto, in accordance with one embodiment of the present patent application.

Referring to FIG. 10, in one embodiment, a shirt 820 includes a neck 822, a first arm 824, a second arm 826, and a central torso section 825 that covers a torso of an individual wearing the shirt. In one embodiment, the shirt 820 has a first sensory strip 838A that is sewn to a first lateral side of the central section 825 and a second sensory strip 838B that is sewn to an opposite, second lateral side of the central section 825. In one embodiment, the shirt 820 may include a third sensory strip 838C that is sewn to a bottom of the central torso section 825. In one embodiment, the third sensory strip 838C is sewn to the front of the shirt at the bottom of the central torso section 825. Each of the first, second and third sensory strips, 838A-838C preferably have inner edges that are sewn to the central torso section 825 of the shirt 820 and free outer edges that may be engaged by an individual's hands and/or fingers to provide sensory feedback and a calming, soothing effect.

Figure 11A:
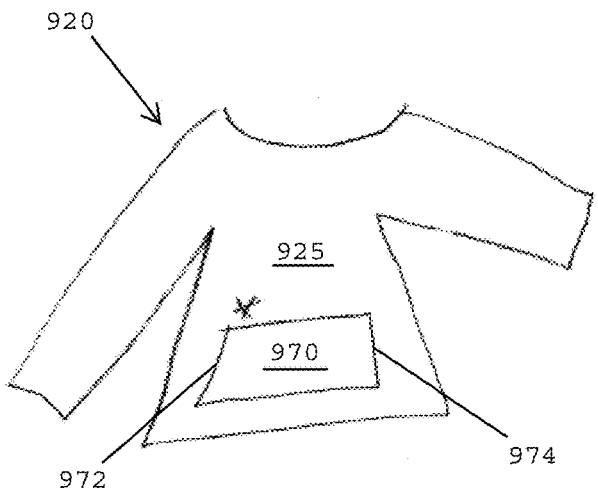
FIGS. 11A and 11B show a shirt having sensory fabric material secured to a front of the shirt, in accordance with embodiment of the present invention.
Figure 11B:
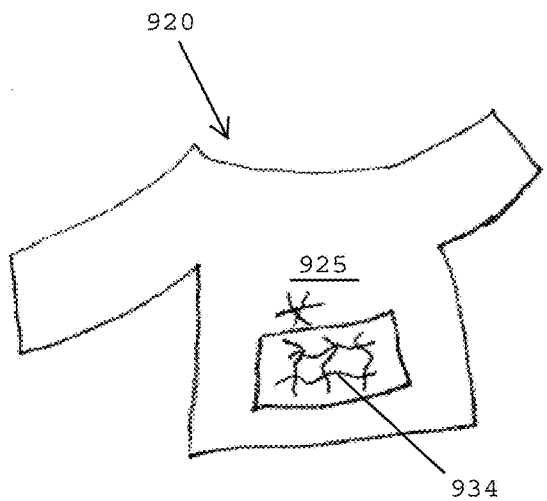

Referring to FIGS. 11A and 11B, in one embodiment, a shirt 920 has a front pocket 970 with side pocket openings 972, 974. In one embodiment, movable fabric material 934 is located inside the front pocket 970. In one embodiment, the movable fabric material 934 may have free edges and desirably projects from the front of the central torso section 925 of the shirt 920. In order to provide a calming effect, an individual may insert his or her hands through the side pocket openings 972, 974 to gain access to the movable fabric material 934 secured to the front of the central torso section 925 of the shirt 920.

Figure 12:
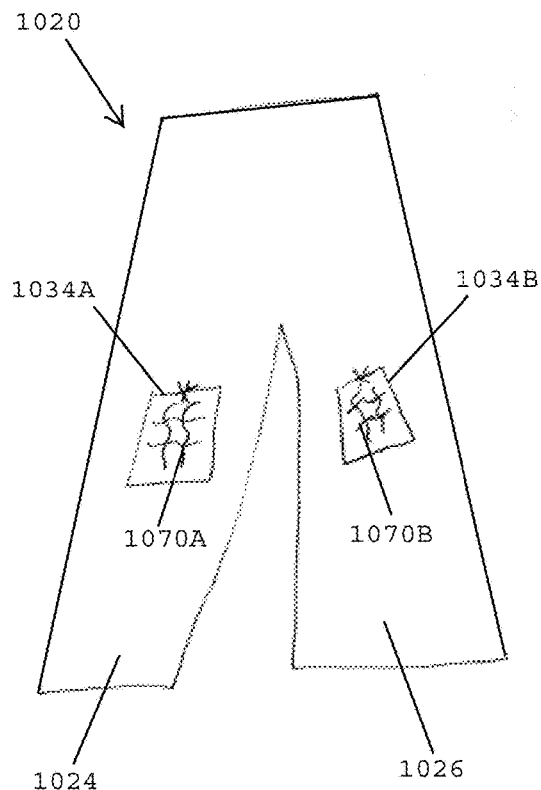
FIG. 12 shows pants having movable sensory fabric added to the outside of knee patches in accordance with one embodiment of the present invention.

Referring to FIG. 12, in one embodiment, pants 1020 may have knee patches 1070A, 1070B sewn over the knees of respective legs 1024, 1026. In one embodiment, each of the knee patches 1070A, 1070B desirably has moveable fabric material 1034A, 1034B projecting therefrom. The movable fabric material 1034A, 1034B may have free edges that may be engaged for providing sensory feedback to obtain a calming, soothing effect.

Figure 13:
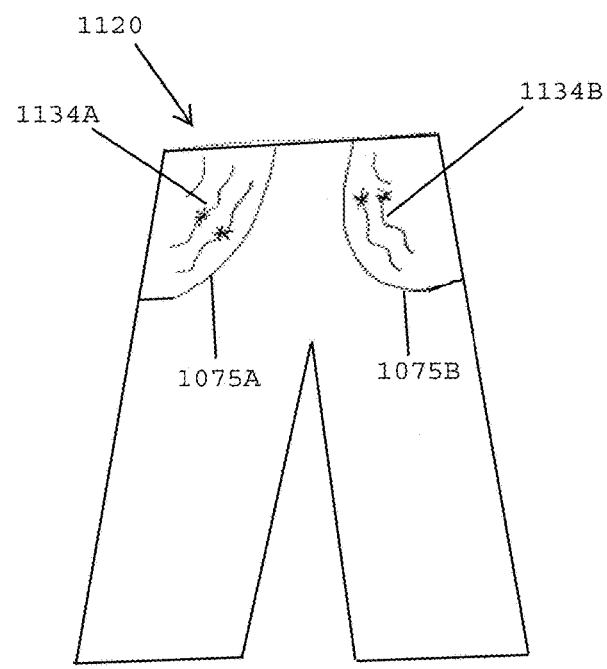
FIG. 13 shows pants having movable sensory fabric material incorporated into pockets of the pants, in accordance with embodiment of the present invention.

Referring to FIG. 13, in one embodiment, pants 1120 preferably include pockets 1175A, 1175B. In one embodiment, each pocket preferably has movable fabric material 1134A, 1134B associated therewith. In one embodiment, the movable fabric material is located inside the pocket so that is not normally seen. In one embodiment, the movable fabric material may be sewn to the outside of the pocket to provide both an ornamental design feature and material that may be engaged by an individual wearing the pants 1120 to provide for sensory feedback and a calming, soothing effect. In one embodiment, one or more of the sensory strips disclosed in the present patent application may be provided inside a pocket to provide a discrete fidget and/or discreet sensory item that may be engaged by an individual wearing a garment. In one embodiment, the discretely located sensory strip may be located along the internal seam of a pocket.

Figure 14:
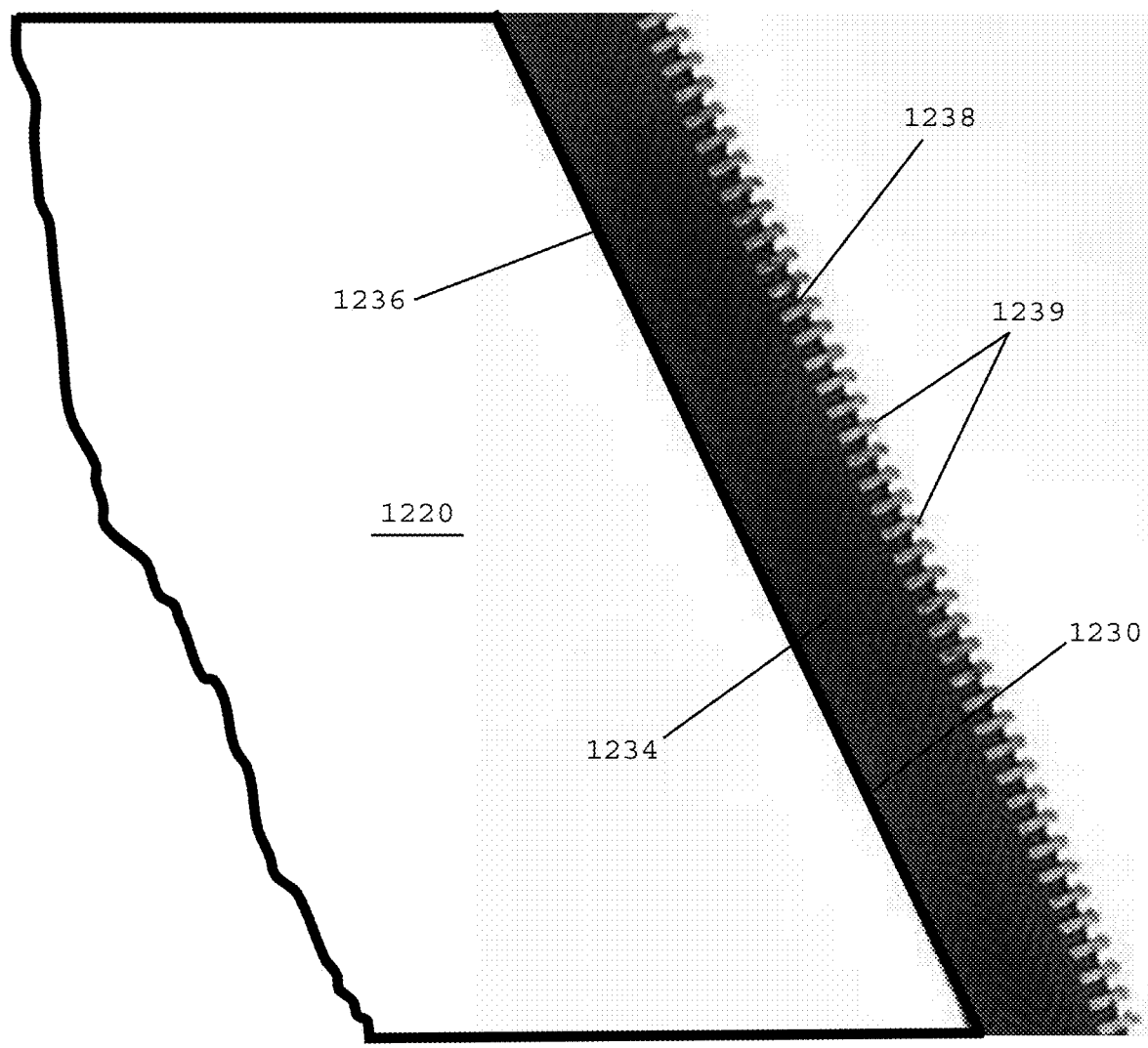
FIG. 14 shows clothing having sensory fabric attached thereto, in accordance with one embodiment of the present patent application.

Referring to FIG. 14, in one embodiment, an article of clothing 1220 may have a sensory strip 1234 sewn to an outer surface 1230 of the clothing. In one embodiment, the sensory strip 1234 has an inner edge 1236 that is sewn to the outer surface 1230 of the article of clothing 1220 and a free outer edge 1238 that includes a roughened element 1239 at the outer edge, which has the appearance and/or look and feel of zipper teeth. Incorporating the roughened element 1239 having the appearance and/or look and feel of zipper teeth provides enhanced tactile feedback for an individual engaging the free outer edge 1238.

Figure 15A:
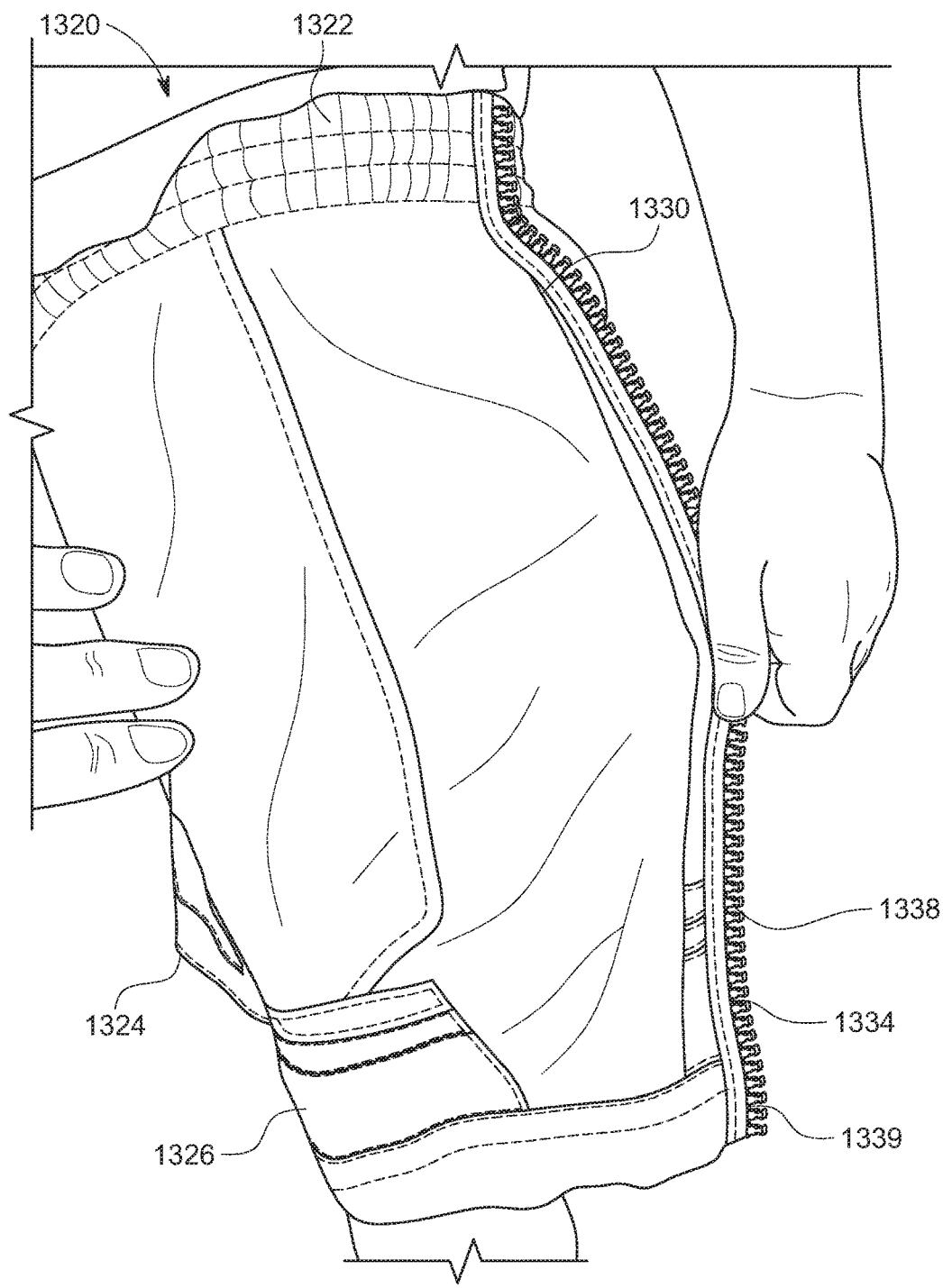
FIG. 15A shows shorts having a sensory strip sewn to the outside of a leg, in accordance with one embodiment of the present patent application.
Figure 15B:
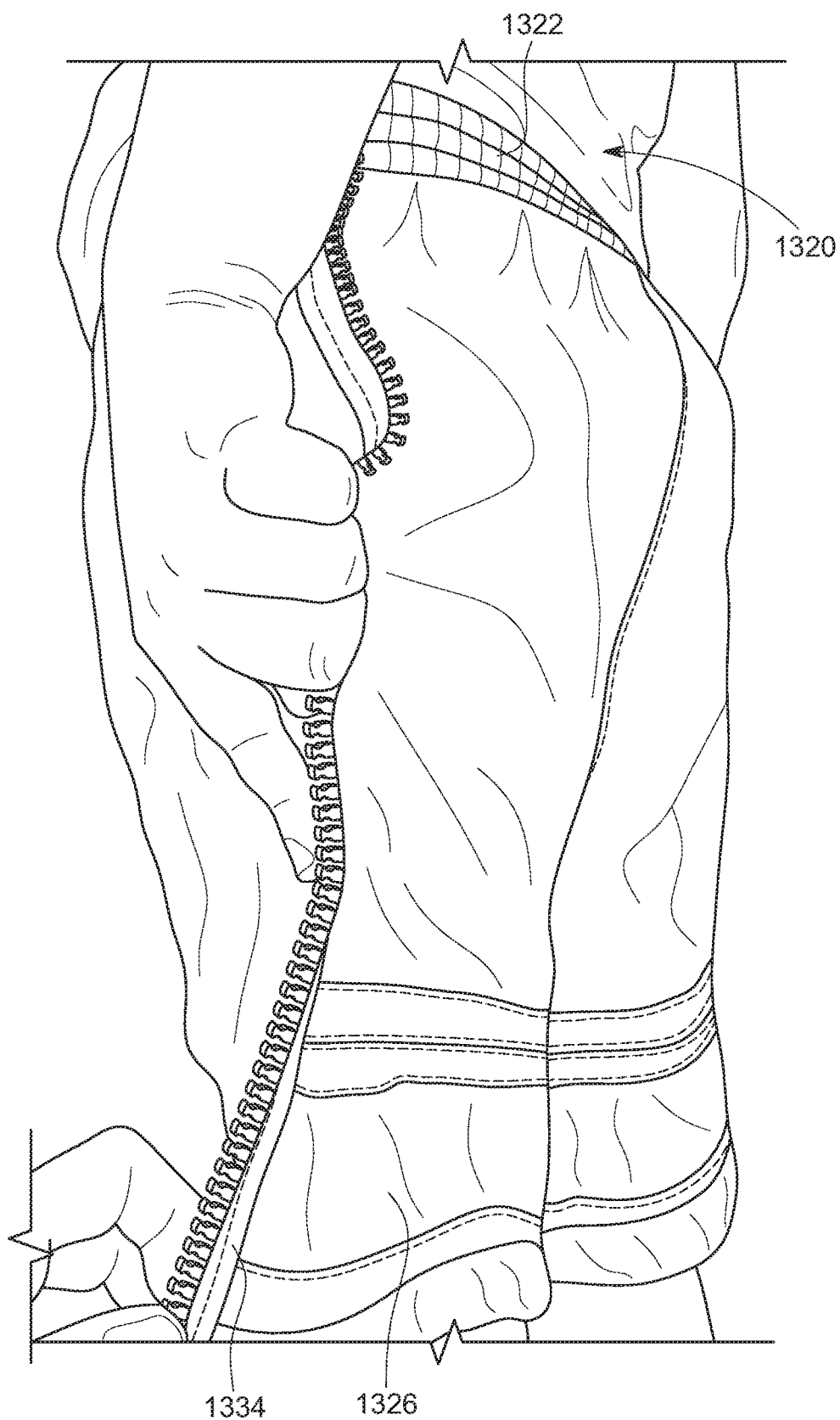
FIG. 15B shows a rear perspective view of the shorts shown in FIG. 15A.

Referring to FIGS. 15A and 15B, in one embodiment, shorts 1320 have a waistband 1322 and legs 1324, 1326 that extend downwardly from the waistband. A sensory strip 1334 having a free outer edge 1338 with a roughened element 1239 having the appearance and/or look and feel of zipper teeth is sewn to the outside surface 1330 of the second leg 1326 of the shorts 1320. The sensory strip 1334 may be similar to that shown and described above in FIG. 14. An individual wearing the shorts 1320 may engage the free outer edge 1338 with hands and/or fingers to provide sensory feedback for obtaining a desired calming effect. In other embodiments, the sensory strip 1334 may be sewn onto pants, shirts, skirts, dresses, swimsuits and all other well-known clothing items.

Figure 16:
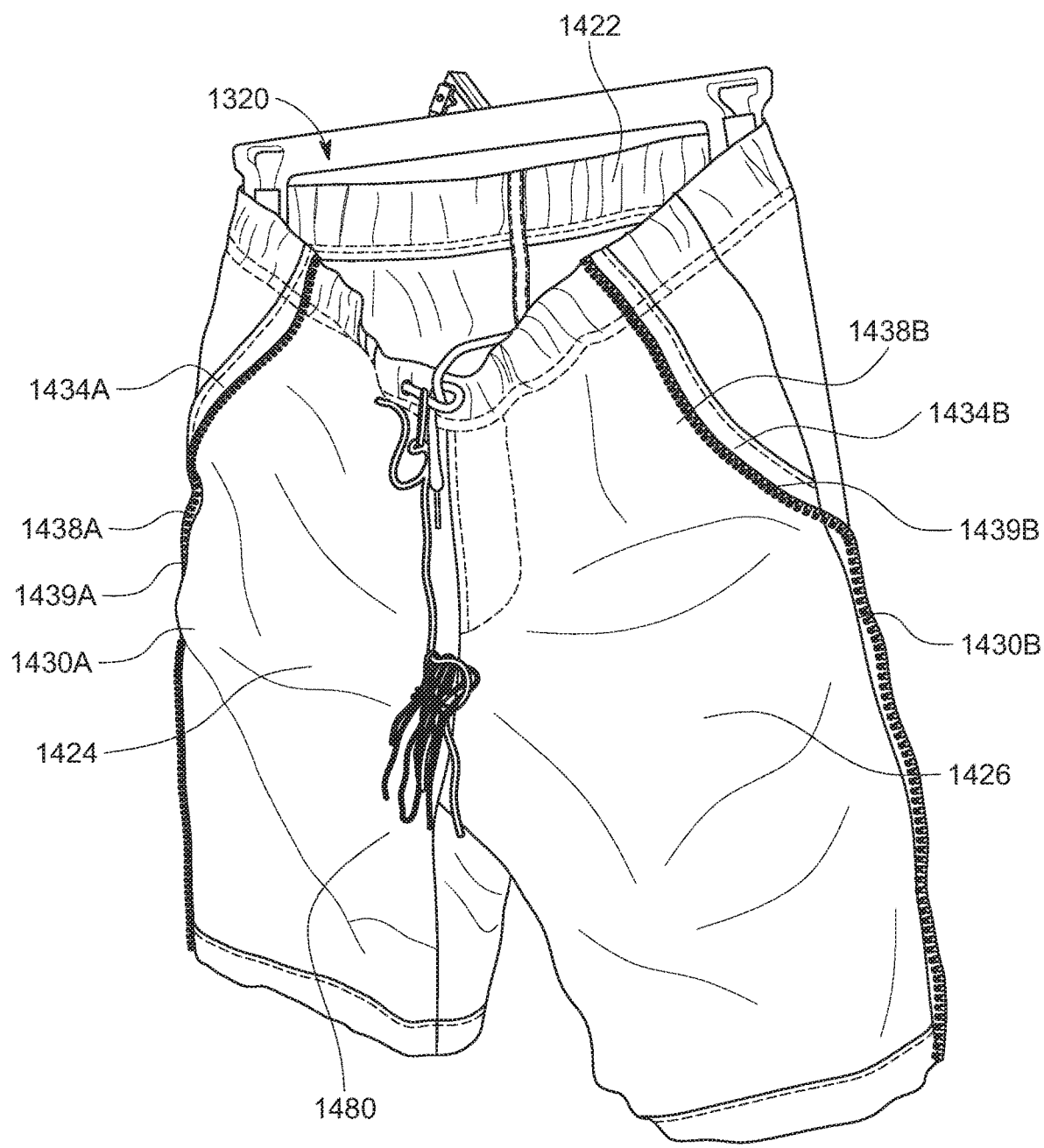
FIG. 16 shows shorts having sensory strips sewn on the legs, in accordance with one embodiment of the present patent application.

Referring to FIG. 16, in one embodiment, shorts 1420 have a waistband 1422 and legs 1424, 1426 that extend downwardly from the waistband. A first sensory strip 1434A having a free outer edge 1438A with a roughened element 1439A having the appearance and/or look and feel of zipper teeth is sewn to the outside surface 1430A of the first leg 1424 of the shorts 1420. In one embodiment, the roughened element 1439A is a continuous molded piece (e.g., a faux zipper half) which minimizes the risk of choking in instances where an individual attempts to detach individual zipper teeth from an edge. A second sensory strip 1434B having a free outer edge 1438B with a roughened element 1439B having the appearance and/or look and feel of zipper teeth is sewn to the outside surface 1430B of the second leg 1426 of the shorts 1420. The sensory strips 1434A, 1434B may be similar to those shown and described above in FIGS. 14, 15A and 15B. An individual wearing the shorts 1420 may engage the roughened elements 1439A, 1439B at the respective free outer edges 1338A and 1338B with hands and/or fingers to provide sensory feedback for obtaining a desired calming effect.

Figure 17:
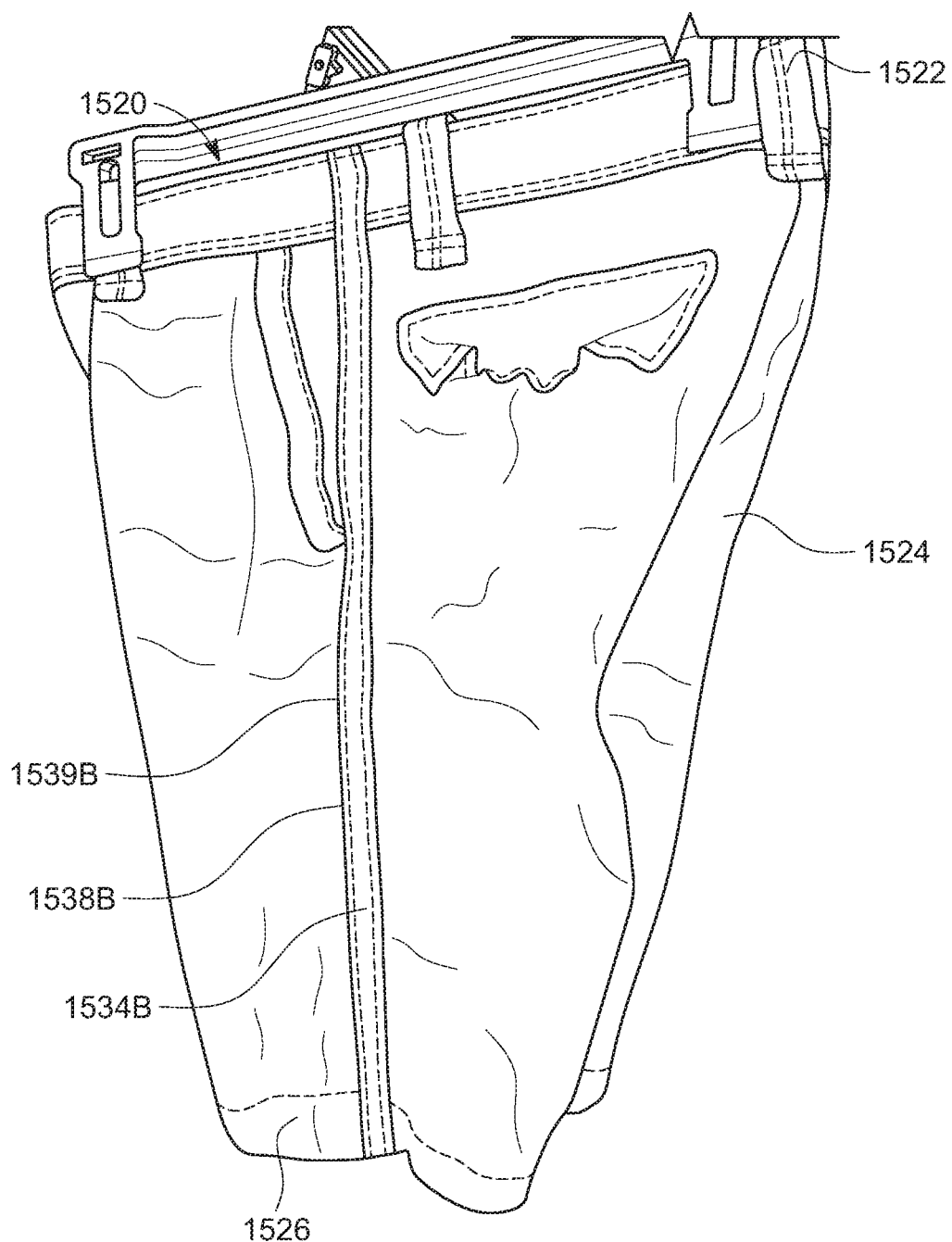
FIG. 17 shows shorts having a sensory strip sewn to the outside of a leg, in accordance with one embodiment of the present patent application.

Referring to FIG. 17, in one embodiment, shorts 1520 have a waistband 1522 and legs 1524, 1526 that extend downwardly from the waistband. A sensory strip 1534B having a free outer edge 1538B with a roughed element 1539B having the appearance and/or look and feel of zipper teeth is sewn to the outside surface 1530B of the second leg 1526 of the shorts 1520. The first leg 1524 may have a similarly constructed sensory strip with a roughened element having the appearance and/or look and feel of zipper teeth sewn thereto. An individual wearing the shorts 1520 may engage the roughened elements and the free outer edge 1538B with hands and/or fingers to provide sensory feedback for obtaining a desired calming effect.

Figures 18A, 18B, 18C:
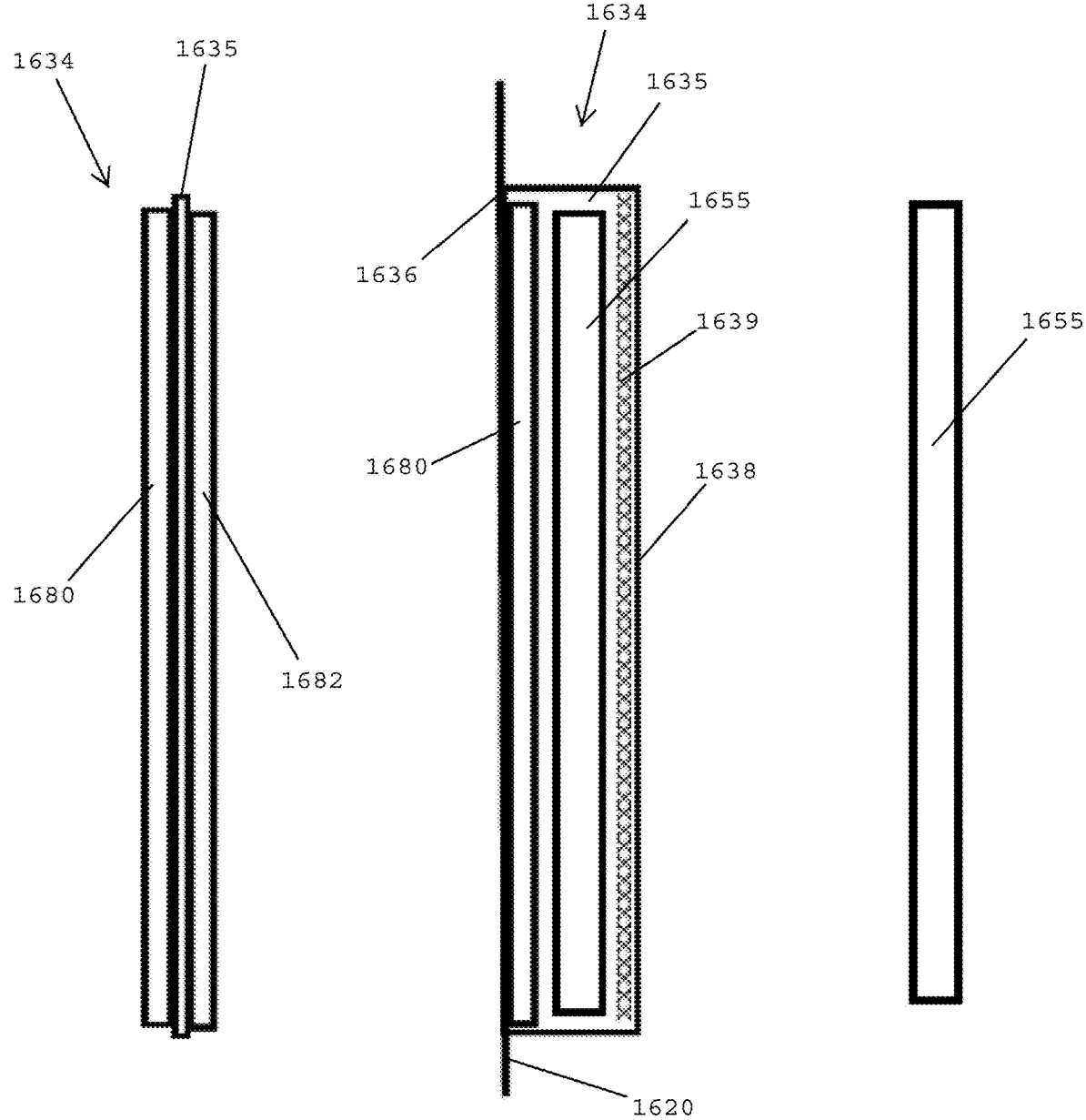
FIG. 18A shows a top plan view of a triple side sensory strip, in accordance with one embodiment of the present patent application.
FIG. 18B shows a side view of the triple sided sensory strip shown in FIG. 18A.
FIG. 18C shows a stiffening element for the triple sided sensory strip shown in FIGS. 18A and 18B.

Referring to FIGS. 18A and 18B, in one embodiment, a sensory strip assembly 1634 for clothing preferably has a first sensory strip 1635 having an inner edge 1636 sewn to an article of clothing 1620 and a free outer edge 1638 that desirably includes supplemental cross stitching 1639 located at the free outer edge. The supplemental cross stitching 1639 preferably makes the free outer edge 1638 stiffer and more durable than portions of the sensory strip 1635 that do not have cross stitching. The sensory strip assembly 1634 preferably includes first and second lateral sensory strips 1680, 1682 that are located on opposite sides of the first sensory strip 1635, and which provide additional surfaces and/or free edges that may be engaged by the hands and/or fingers of an individual wearing clothing having the sensory strip assembly 1634 incorporated therein.

Referring to FIG. 18C, in one embodiment, a stiffening element 1655 may be incorporated into a sensory strip. The stiffening element 1655 may be elongated and may approximate the length of the sensory strip. In one embodiment, the stiffening element 1655 may be made of durable materials such as plastic, polymers, metal, wood, cellulose and fiber. FIG. 18B shows the stiffening element 1655 incorporated into the first sensory strip 1635. In one embodiment, the stiffening element 1655 desirably adds stiffness to the free outer edge 1638 of the first sensory strip 1635. The stiffening element may float inside the first sensory strip or may be held in place by stitching that passes through the first sensory strip.

Figure 19A:
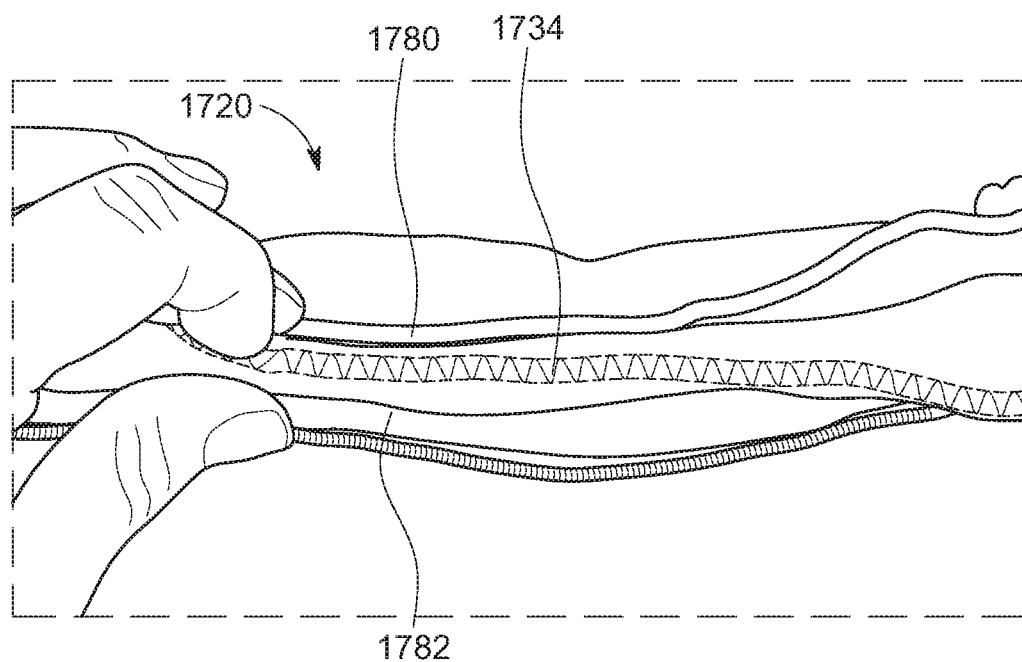
FIG. 19A shows a top perspective view of a triple sided sensory strip, in accordance with one embodiment of the present patent application.
Figure 19B:
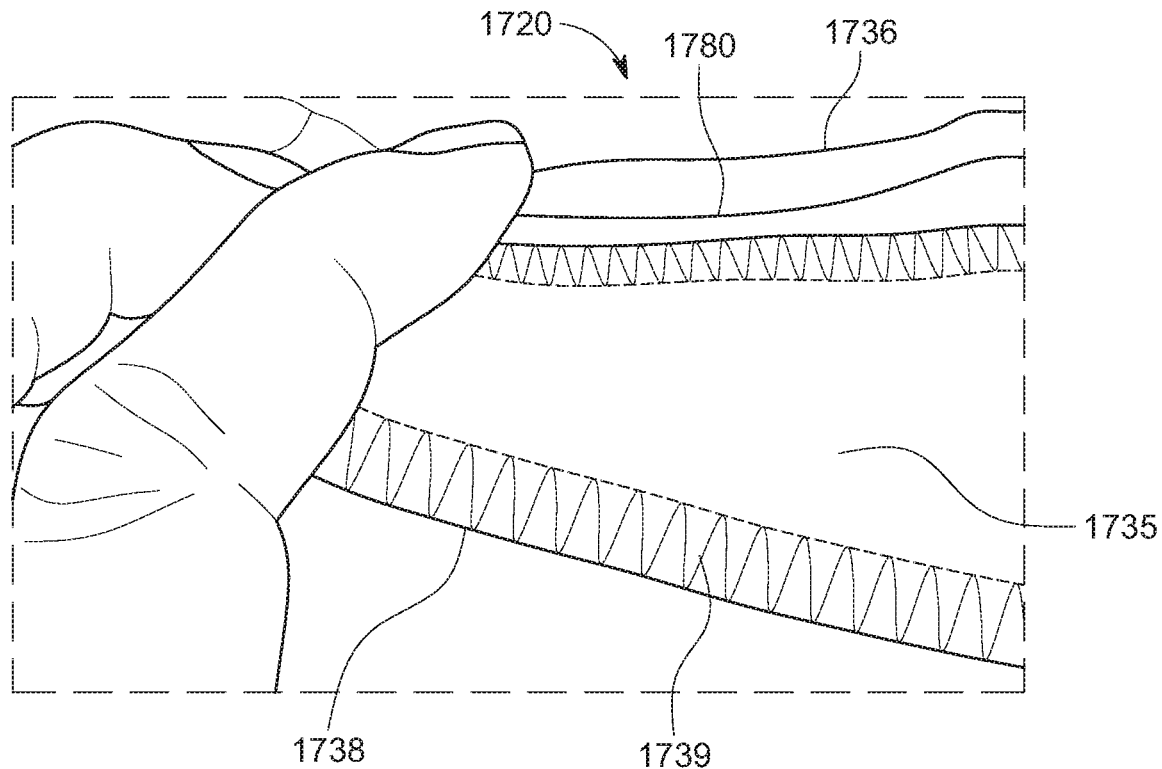
FIG. 19B shows a right side perspective view of the triple sided sensory strip shown in FIG. 19A.

Referring to FIGS. 19A and 19B, in one embodiment, an article of clothing 1720 has a sensory strip assembly 1734 sewn thereto. The sensory strip assembly 1734 preferably has a first sensory strip 1735 having an inner edge 1736 sewn to the article of clothing 1720 and a free outer edge 1738 that desirably includes supplemental cross stitching 1739 located at the free outer edge. The supplemental cross stitching 1739 preferably makes the free outer edge 1738 stiffer and more durable than portions of the first sensory strip 1735 that do not have cross stitching. The sensory strip assembly 1734 preferably includes first and second lateral sensory strips 1780, 1782 that are located on opposite sides of the first sensory strip 1735, and which provide additional surfaces and/or free edges that may be engaged by the hands and/or fingers of an individual wearing clothing having the sensory strip assembly 1734 incorporated therein. In one embodiment, an elongated stiffening element such as an elongated piece of plastic or polymer material may be incorporated into the first sensory strip to stiffen the first sensory strip. The elongated stiffening element may be held in place by the supplemental cross stitching 1739.

Figure 20A:
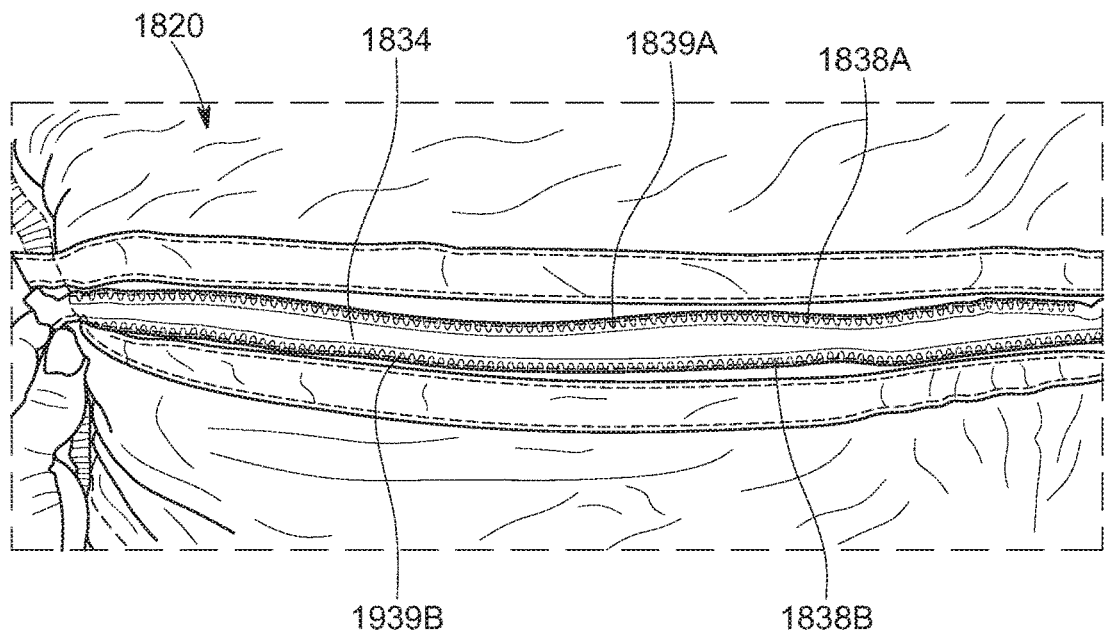
FIG. 20A shows a top plan view of a double sided sensory strip, in accordance with one embodiment of the present patent application.
Figure 20B:
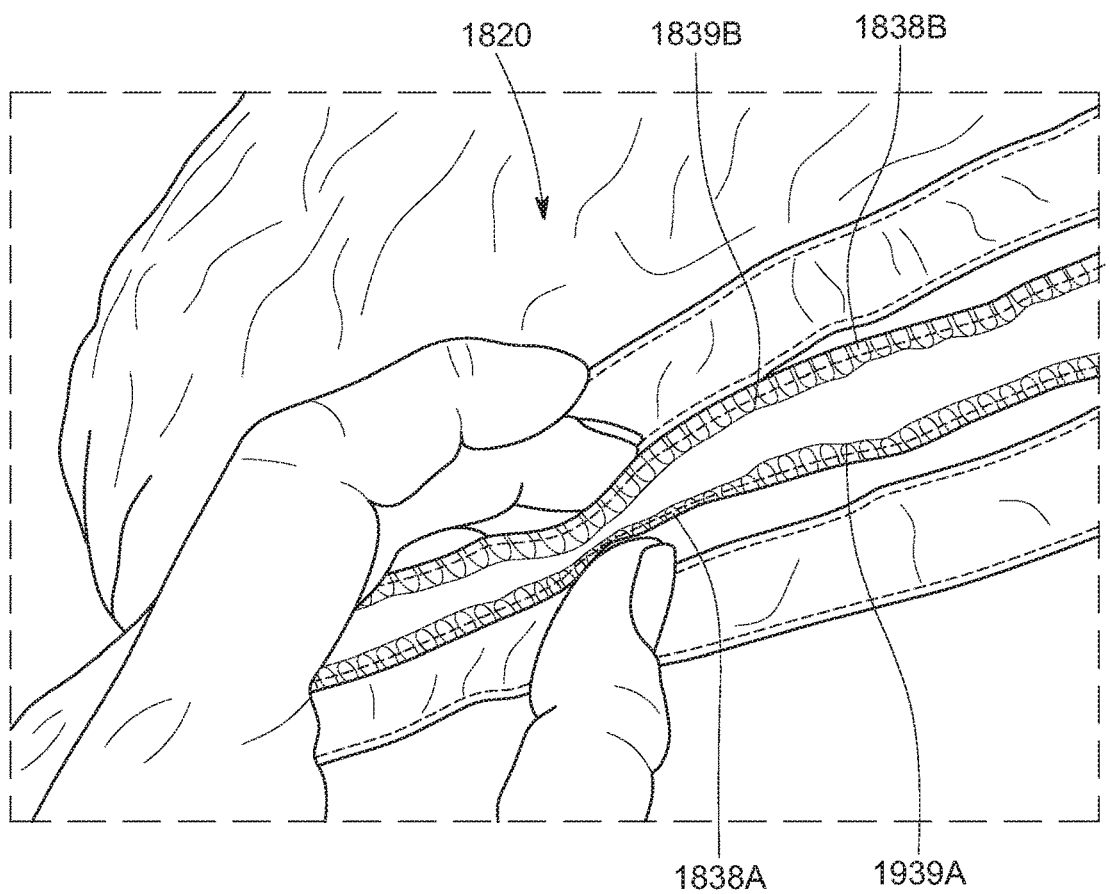
FIG. 20B shows a perspective view of the double side sensory strip of FIG. 20A.

Referring to FIGS. 20A and 20B, in one embodiment, an article of clothing 1820 has a double sided sensory strip 1834 sewn thereto. A central section of the strip 1834 is sewn to an outer surface of the clothing 1820. In one embodiment, the double sided sensory strip 1834 preferably has first and second free outer edges 1838A, 1838B, whereby each outer edge has supplemental cross stitching 1839A, 1839B. The supplemental cross stitching 1839A, 1839B preferably makes the free outer edges 1838A, 1838B stiffer and more durable than portions of the sensory strip 1834 that do not have cross stitching. The free outer edges 1838A, 1838B are preferably engaged by an individual wearing the article of clothing 1820 (e.g., with fingers rubbing over the edges) to provide sensory feedback for obtaining a calming, soothing effect.

Figure 21A:
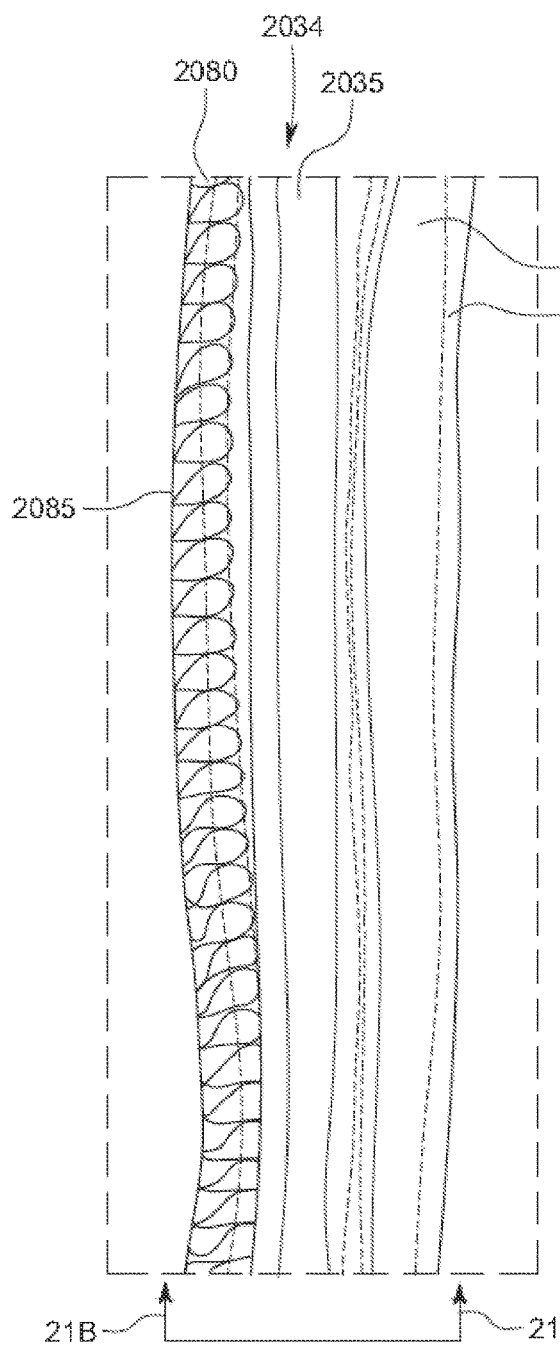
FIG. 21A shows a top plan view of a sensory strip assembly, in accordance with one embodiment of the present patent application.
Figure 21B:
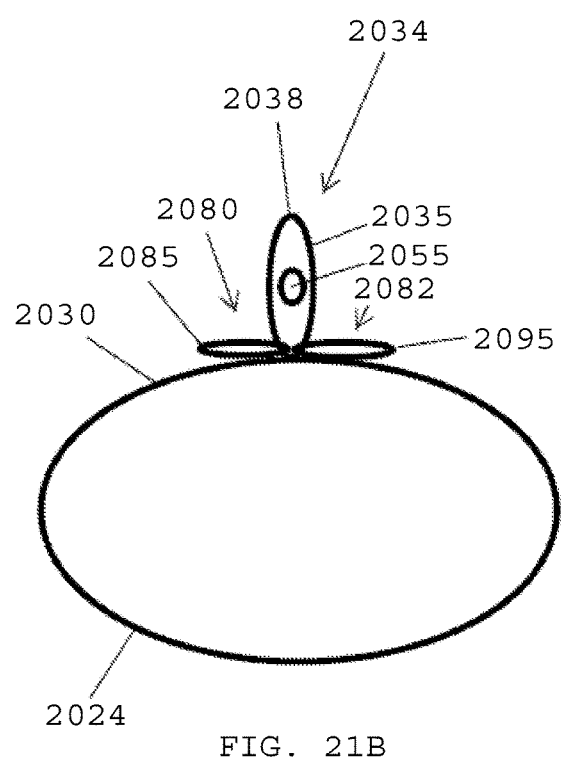
FIG. 21B shows a cross-sectional view of the sensory strip assembly of FIG. 21A.

Referring to FIGS. 21A and 21B, in one embodiment, a sensory strip assembly 2034 for clothing preferably has a central sensory strip 2035 having an inner edge 2036 sewn to an outer surface 2030 of a leg 2024 of an article of clothing 2020 and a free outer edge 2038. In one embodiment, the central sensory strip 2035 contains an elongated stiffening element 2055 that is free to float and/or move inside the central sensory strip. The elongated stiffening element 2055 may be a string or twine that is disposed inside the central sensory strip 2035. In one embodiment, the elongated stiffening element 2055 may be made of durable materials such as plastic, polymers, metal, wood, cellulose and fiber. In one embodiment, the elongated stiffening element 2055 desirably adds stiffness to the free outer edge 2038 of the central sensory strip 2035.

In one embodiment, the sensory strip assembly 2034 desirably includes first and second lateral sensory strips 2080, 2082 that are located on opposite sides of the central sensory strip 2035, that have inner edges sewn to the outer surface 2030 of the leg 2024, and which provide additional surfaces and/or free edges that may be engaged by the hands and/or fingers of an individual wearing clothing having the sensory strip assembly 2034 incorporated therein. In one embodiment, the first lateral sensory strip 2080 preferably has a free outer edge 2085 with cross-stitching and/or a surged edge that adds stiffness to the free outer edge 2085. In one embodiment, the second lateral sensory strip 2082 has a free outer edge 2095 having a hemmed edge. The three outer edges of the respective sensory strips 2035, 2080, and 2082 have different structural features to provide three different modes of sensory feedback to an individual engaging the free edges with hands and/or fingers.

Figure 22A:
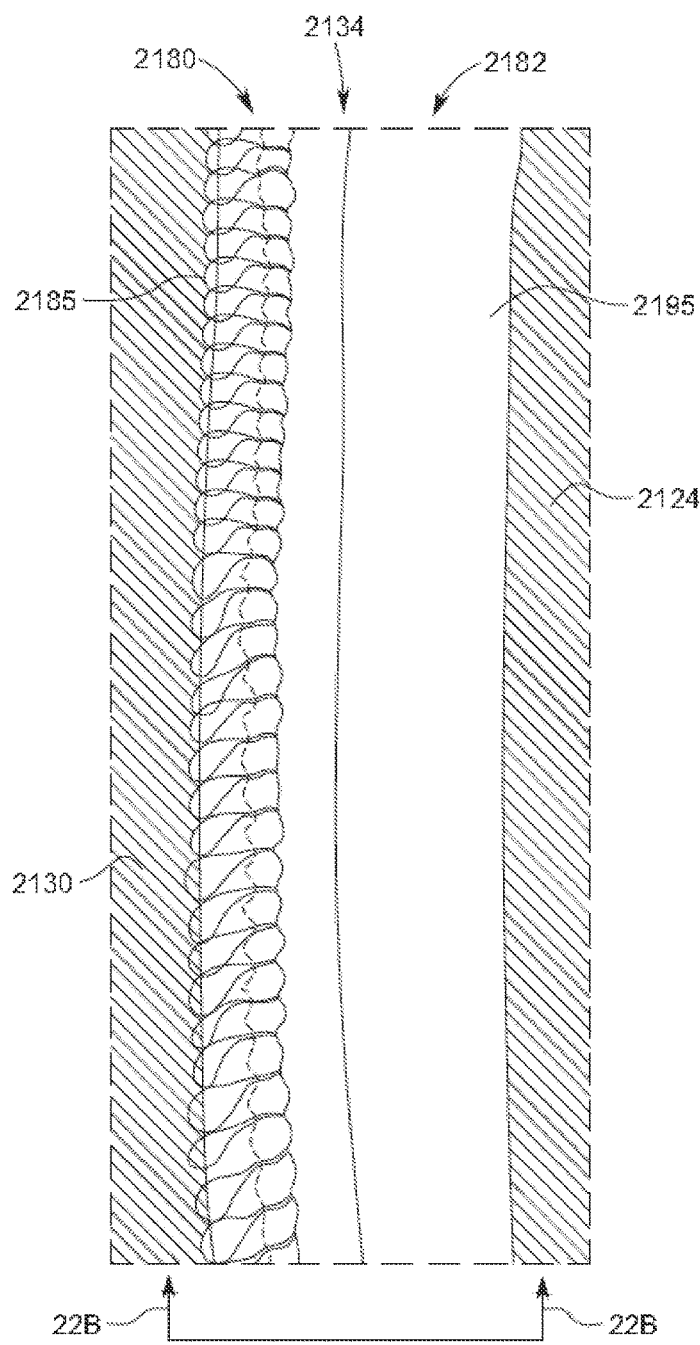
FIG. 22A shows a top plan view of a sensory strip assembly, in accordance with one embodiment of the present patent application.
Figure 22B:
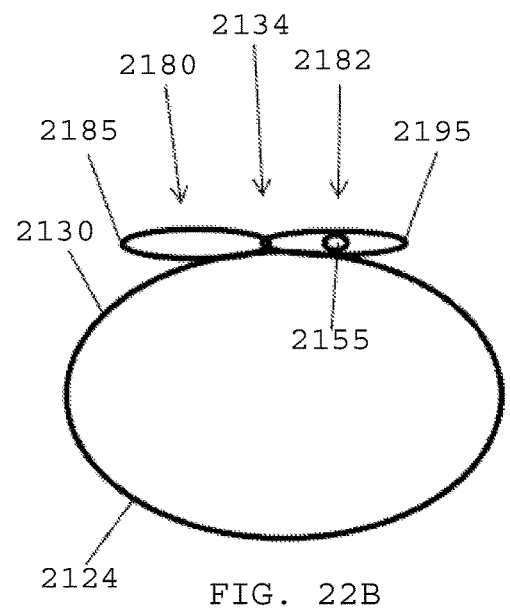
FIG. 22B shows a cross-sectional view of the sensory strip assembly of FIG. 22A.

Referring to FIGS. 22A and 22B, in one embodiment, a sensory strip assembly 2134 for clothing preferably has first and second laterally extending sensory strips 2180, 2182 having inner edges sewn to the outer surface 2130 of a leg 2124 of an article of clothing and respective free outer edges 2185, 2195 that may be engaged by the hands and/or fingers of an individual wearing clothing having the sensory strip assembly 2134 incorporated therein. In one embodiment, the first laterally extending sensory strip 2180 preferably has a free outer edge 2185 with cross-stitching and/or a surged edge that adds stiffness to the free outer edge 2185. In one embodiment, the second laterally extending sensory strip 2182 has a free outer edge 2195. In one embodiment, the second laterally extending sensory strip 2182 contains an elongated stiffening element 2155 that is free to float and/or move inside the central sensory strip. The elongated stiffening element 2155 may be a string or twine that is disposed inside the second laterally extending sensory strip 2135. In one embodiment, the elongated stiffening element 2155 may be made of durable materials such as plastic, polymers, metal, wood, cellulose and fiber. In one embodiment, the elongated stiffening element 2155 desirably adds stiffness to the free outer edge 2195 of the second laterally extending sensory strip 2182. In one embodiment, the second sensory strip 2182 may have stitches passing therethrough for holding the elongated stiffening element in place so that it may not move around inside the second sensory strip. In one embodiment, the elongated element may be flat or may have a tubular shape.

Figure 23A:
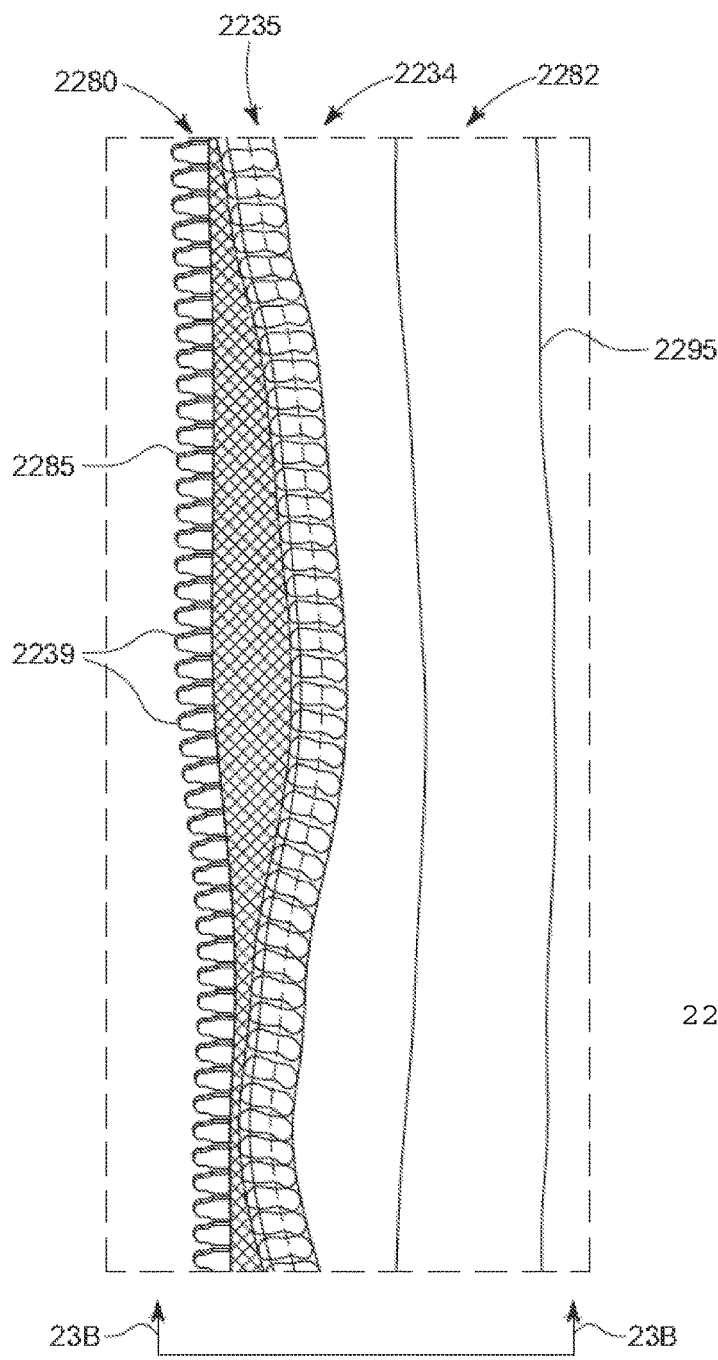
FIG. 23A shows a top plan view of a sensory strip assembly, in accordance with one embodiment of the present patent application.
Figure 23B:
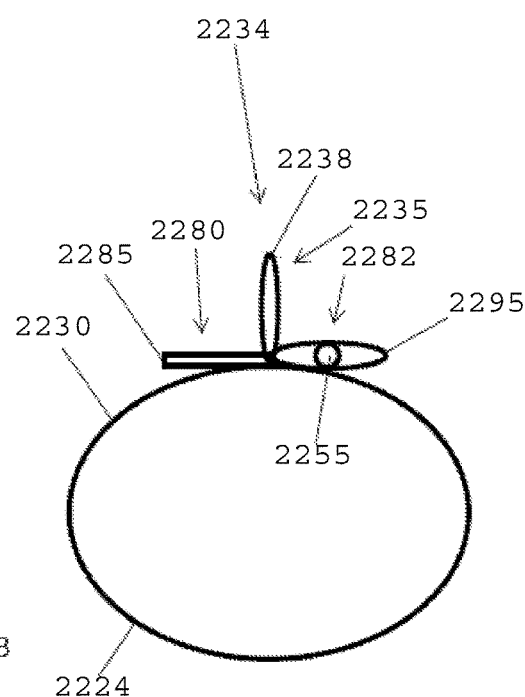
FIG. 23B shows a cross-sectional view of the sensory strip assembly of FIG. 23A.

Referring to FIGS. 23A and 23B, in one embodiment, a sensory strip assembly 2234 for clothing preferably has a central sensory strip 2235 having an inner edge 2236 sewn to an outer surface 2230 of a leg 2224 of an article of clothing and a free outer edge 2238. In one embodiment, the free outer edge 2238 has cross-stitching and/or a surged edge that adds stiffness to the free outer edge of the central sensory strip 2235.

In one embodiment, the sensory strip assembly 2234 desirably includes first and second lateral sensory strips 2280, 2282 that are located on opposite sides of the central sensory strip 2235, that have inner edges sewn to the outer surface 2230 of the leg 2224, and which provide additional surfaces and/or free edges that may be engaged by the hands and/or fingers of an individual wearing clothing having the sensory strip assembly 2234 incorporated therein.

In one embodiment, the first lateral sensory strip 2280 has an inner edge that is sewn to the outer surface of the leg 2224 and a free outer edge 2285 that includes a roughened element 2239 (FIG. 23A) at the free outer edge, which has the appearance and/or look and feel of zipper teeth. Incorporating the roughened element 2239 having the appearance and/or look and feel of zipper teeth provides enhanced tactile feedback for an individual engaging the free outer edge 2285 of the first lateral sensory 2280.

In one embodiment, the second lateral sensory strip 2282 contains an elongated stiffening element 2255 that is free to float and/or move inside the second lateral sensory strip. The elongated stiffening element 2255 may be a string or twine that is disposed inside the second lateral sensory strip 2282. In one embodiment, the elongated stiffening element 2255 may be made of durable materials such as plastic, polymers, metal, wood, cellulose and fiber. In one embodiment, the elongated stiffening element 2255 provides an additional sensory input device for engagement with hands and/or fingers desirably adds stiffness to the free outer edge 2295 of the second lateral sensory strip 2282.

Figures 24A, 24B:
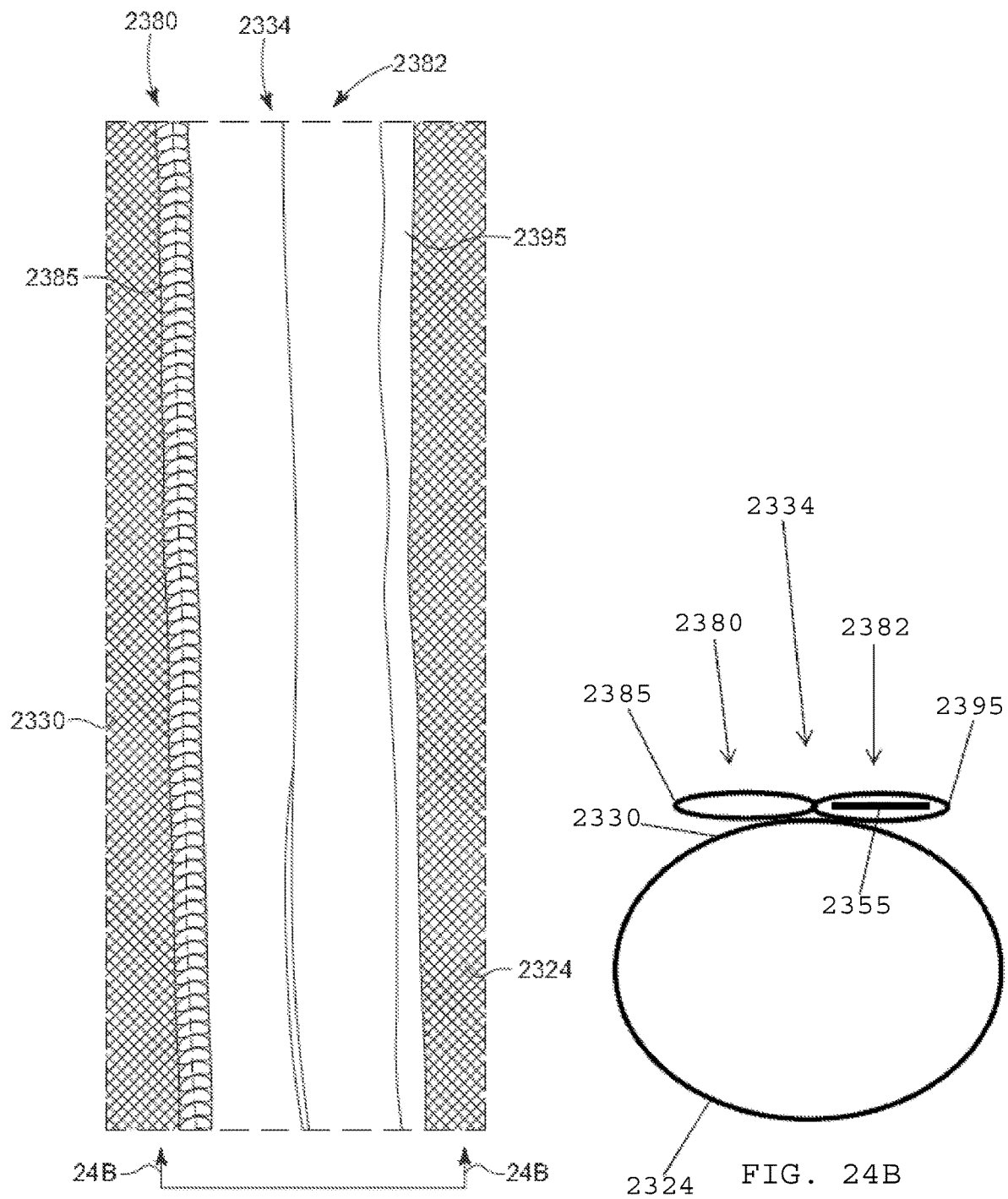
FIG. 24A shows a top plan view of a sensory strip assembly, in accordance with one embodiment of the present patent application.
FIG. 24B shows a cross-sectional view of the sensory strip assembly of FIG. 24A.

Referring to FIGS. 24A and 24B, in one embodiment, a sensory strip assembly 2334 for clothing preferably has first and second laterally extending sensory strips 2380, 2382 having inner edges sewn to the outer surface 2330 of a leg 2324 of an article of clothing and respective free outer edges 2385, 2395 that may be engaged by the hands and/or fingers of an individual wearing clothing having the sensory strip assembly 2334 incorporated therein. In one embodiment, the first laterally extending sensory strip 2380 preferably has a free outer edge 2385 with cross-stitching and/or a surged edge that adds stiffness to the free outer edge 2385. In one embodiment, the second laterally extending sensory strip 2382 has a free outer edge 2395. In one embodiment, the second laterally extending sensory strip 2382 contains an elongated, flat stiffening element 2355 that is disposed inside the second laterally extending sensory strip 2382. The elongated, flat stiffening element 2355 may be made of durable materials such as plastic, polymers, metal, wood, cellulose and fiber. In one embodiment, the elongated, flat stiffening element 2355 desirably adds stiffness to the free outer edge 2395 of the second laterally extending sensory strip 2382. In one embodiment, the second laterally extending sensory strip 2382 may have stitches passing therethrough for holding the elongated, flat stiffening element 2355 in place so that it may not move around inside the second laterally extending sensory strip 2382. In one embodiment, the elongated, flat stiffening element 2355 may be similar to that shown and described above in FIGS. 18A-18C.

Figure 25A:
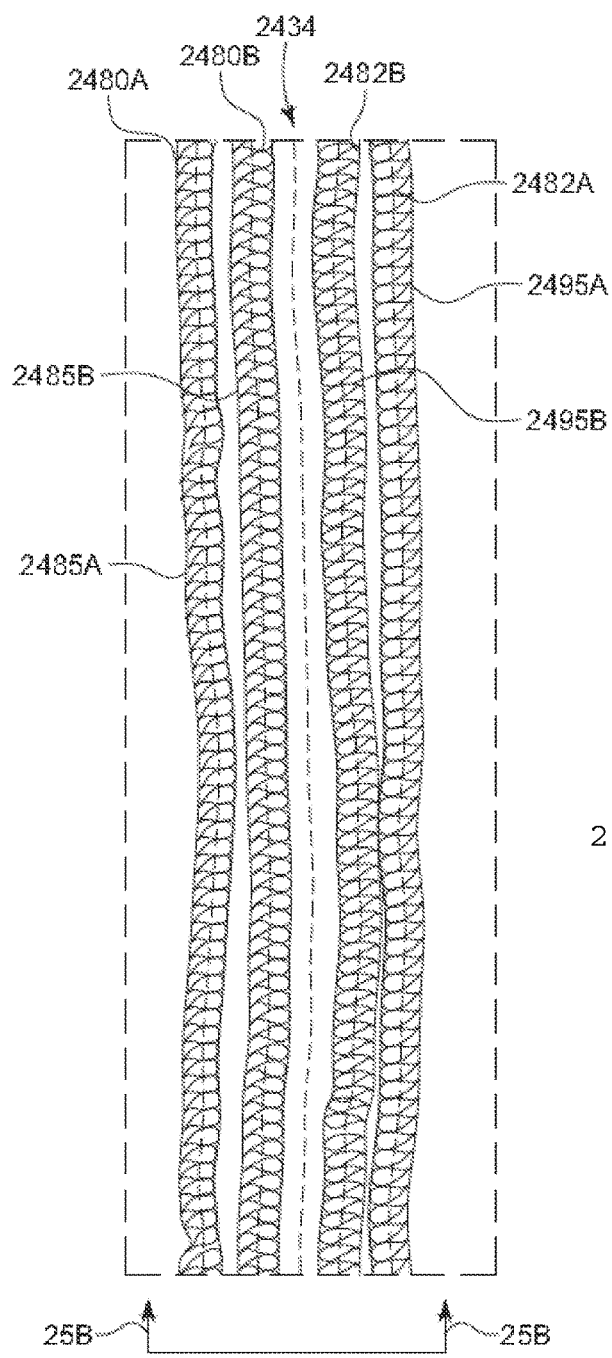
FIG. 25A shows a top plan view of a sensory strip assembly, in accordance with one embodiment of the present patent application.
Figure 25B:
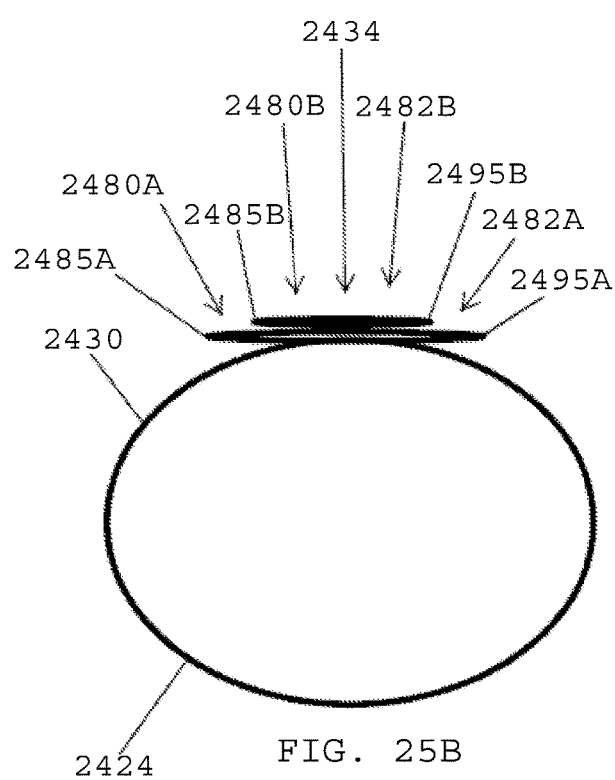
FIG. 25B shows a cross-sectional view of the sensory strip assembly of FIG. 25A.

Referring to FIGS. 25A and 25B, in one embodiment, a sensory strip assembly 2434 for clothing preferably has first and second outer laterally extending sensory strips 2480A, 2482A having inner edges sewn to the outer surface 2430 of a leg 2424 of an article of clothing and respective free outer edges 2485A, 2495A that may be engaged by the hands and/or fingers of an individual wearing clothing having the sensory strip assembly 2434 incorporated therein. In one embodiment, the sensory strip assembly 2434 for clothing preferably has first and second inner laterally extending sensory strips 2480B, 2482B having inner edges sewn to the outer surface 2430 of a leg 2424 of an article of clothing and respective free outer edges 2485B, 2495B that may be engaged by the hands and/or fingers of an individual wearing clothing having the sensory strip assembly 2434 incorporated therein. In one embodiment, free outer edges of the four sensory strips have cross-stitching and/or a surged edge that adds stiffness to the free outer edges 2485A, 2485B, 2495A, and 2495B.

Referring to FIGS. 26A and 26B, in one embodiment, a sensory strip assembly 2534 for clothing preferably has first and second outer laterally extending sensory strips 2580A, 2582A having inner edges sewn to the outer surface 2530 of a leg 2524 of an article of clothing and respective free outer edges 2585A, 2595A that may be engaged by the hands and/or fingers of an individual wearing clothing having the sensory strip assembly 2534 incorporated therein. In one embodiment, the sensory strip assembly 2534 for clothing preferably has first and second inner laterally extending sensory strips 2580B, 2582B having inner edges sewn to the outer surface 2530 of a leg 2524 of an article of clothing and respective free outer edges 2585B, 2595B that may be engaged by the hands and/or fingers of an individual wearing clothing having the sensory strip assembly 2534 incorporated therein. In one embodiment, the sensory strip assembly 2534 for clothing preferably has first and second intermediate laterally extending sensory strips 2580C, 2582C having inner edges sewn to the outer surface 2530 of a leg 2524 of an article of clothing and respective free outer edges 2585C, 2595C that may be engaged by the hands and/or fingers of an individual wearing clothing having the sensory strip assembly 2534 incorporated therein. In one embodiment, free outer edges of the six sensory strips have cross-stitching and/or a surged edge that adds stiffness to the free outer edges 2585A, 2585B, 2585C, 2595A, 2595B, and 2595C.

Figures 27A, 27B:
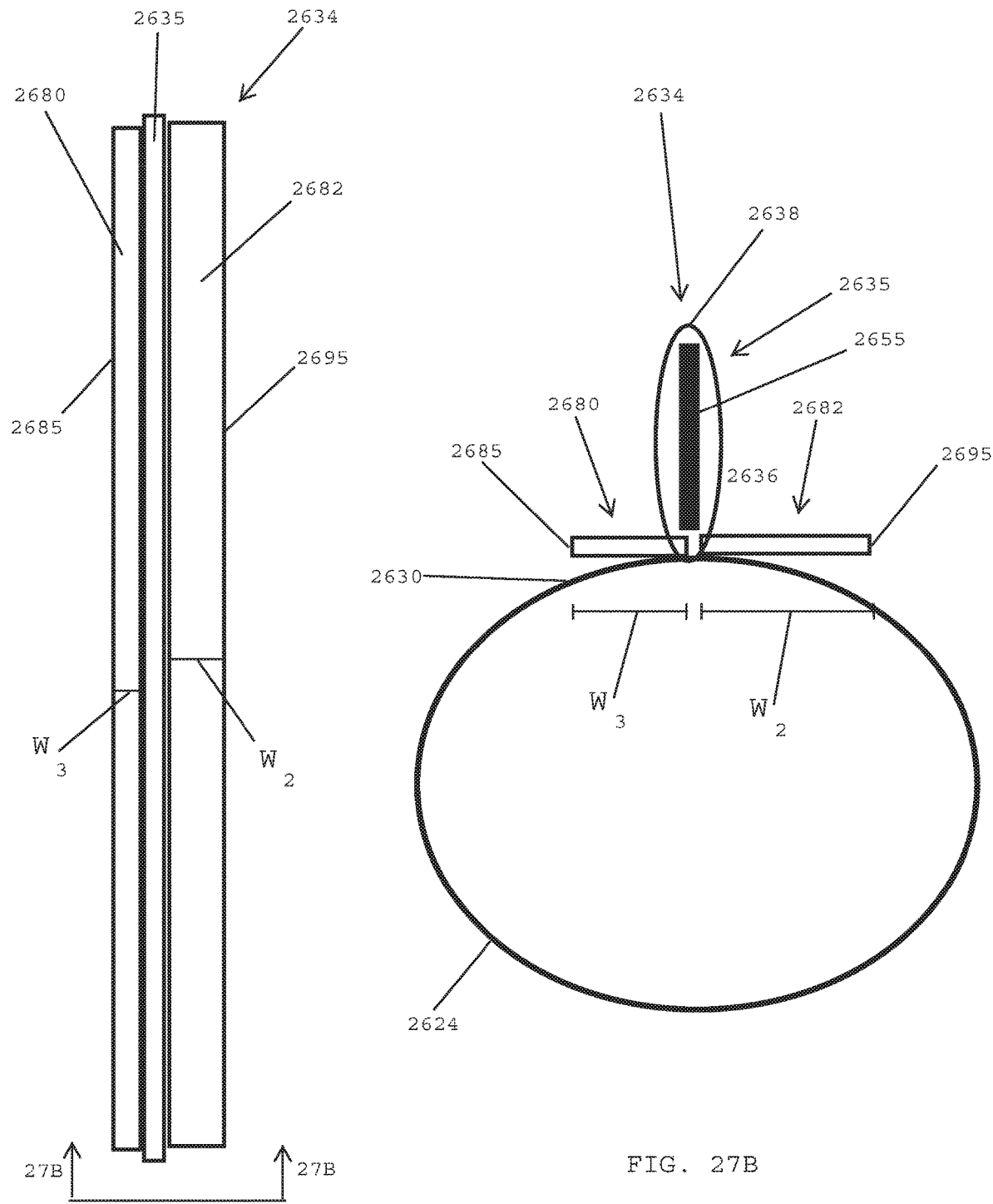
FIG. 27A shows a top plan view of a sensory strip assembly, in accordance with one embodiment of the present patent application.
FIG. 27B shows a cross-sectional view of the sensory strip assembly of FIG. 27A.

Referring to FIGS. 27A and 27B, in one embodiment, a sensory strip assembly 2634 for clothing preferably has a central sensory strip 2635 having an inner edge 2636 sewn to an outer surface 2630 of a leg 2624 of an article of clothing and a free outer edge 2638. In one embodiment, the central sensory strip 2635 contains an elongated, flat stiffening element 2655 embedded therein. In one embodiment, the elongated, flat stiffening element 2655 may be made of durable materials such as plastic, polymers, metal, wood, cellulose and fiber. In one embodiment, the elongated, flat stiffening element 2655 desirably adds stiffness to the free outer edge 2638 of the central sensory strip 2635 and/or provides an additional element that may be engaged for providing sensory feedback.

In one embodiment, the sensory strip assembly 2634 desirably includes first and second lateral sensory strips 2680, 2682 that are located on opposite sides of the central sensory strip 2635, that have inner edges sewn to the outer surface 2630 of the leg 2624, and which provide additional surfaces and/or free edges that may be engaged by the hands and/or fingers of an individual wearing clothing having the sensory strip assembly 2634 incorporated therein. In one embodiment, the first lateral sensory strip 2680 preferably has a free outer edge 2685 with cross-stitching and/or a surged edge that adds stiffness to the free outer edge 2685. In one embodiment, the second lateral sensory strip 2682 has a free outer edge 2695 with cross-stitching and/or a surged edge that adds stiffness to the free outer edge 2695. In one embodiment, the second lateral sensory strip 2682 has a width $W_2$ that is greater than the width $W_3$ of the first lateral sensory strip 2680. In one embodiment, the three sensory strips 2635, 2680, and 2682 have different structural features to provide three different modes of sensory feedback to an individual engaging the free edges with hands and/or fingers.

In one embodiment, any of the sensory strips disclosed herein may be releasably secured to any of the clothing items disclosed herein, such as the leg of pants. As used herein, the terminology "releasably secured" means that a sensory strip is not permanently affixed to and/or sewn to a clothing item, but that the sensory strip may be selectively secured to a clothing item using a fastening system and then selectively detached from the clothing item, if desired. The fastening system preferably enables sensory strips to be repeatedly attached and detached from clothing without damaging or destroying the sensory strips, the clothing and/or the components of the fastening system. Various fastening system structures may be used for "releasably attaching" a sensory strip to clothing including using zippers, zipper teeth, hook and loop fastener strips (e.g., VELCO® material), buttons, snaps, magnets and laces. In one embodiment, a sensory strip may be removed (e.g., unzipped) from clothing for laundering the clothing and/or the sensory strip, and the sensory strip may be re-attached to the clothing after the clothing and/or the sensory strip has been laundered (e.g., washed and dried). In one embodiment, an individual may have a preferred sensory strip that he or she desires to wear on different clothes. In one embodiment, a sensory strip may be transferred to a particular clothing item that an individual is wearing for that day. For example, in the morning, a preferred sensory strip may be secured to pants for use during a school day. In the afternoon, after school, the preferred sensory strip may be detached from the pants and releasably attached to another clothing item such as shorts for after school play.

Figure 28A:
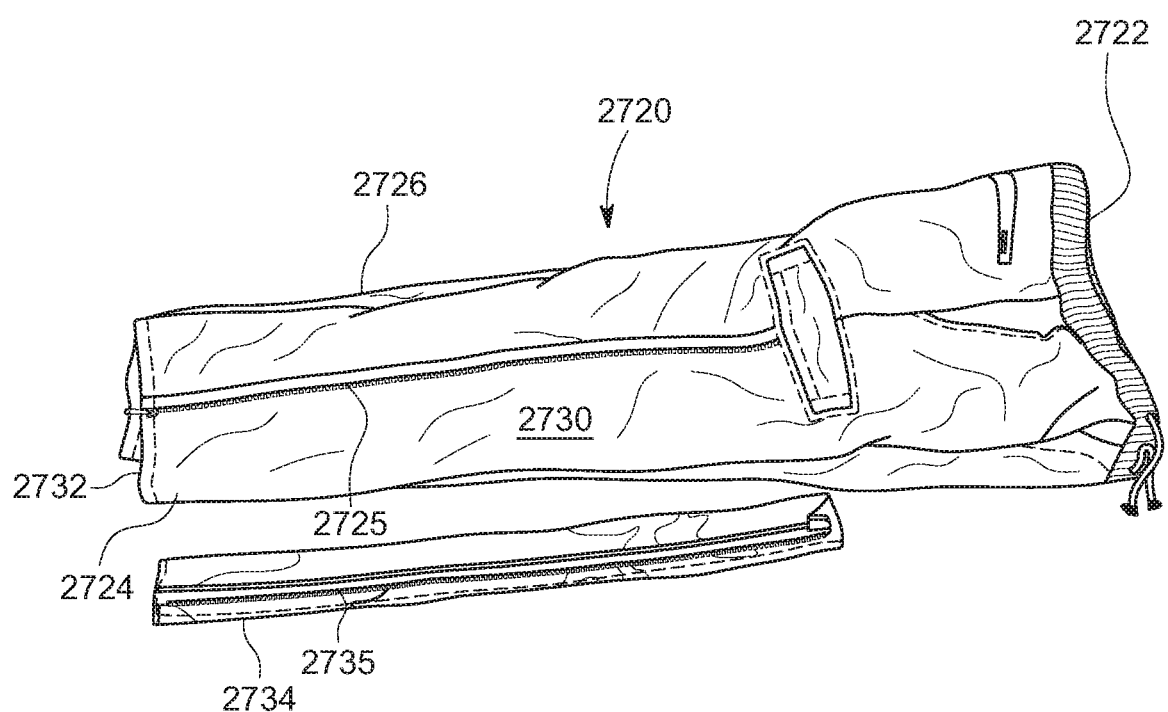
FIG. 28A shows pants and a sensory strip that is adapted to be releasably attached to a leg of the pants, in accordance with one embodiment of the present patent application.
Figure 28B:
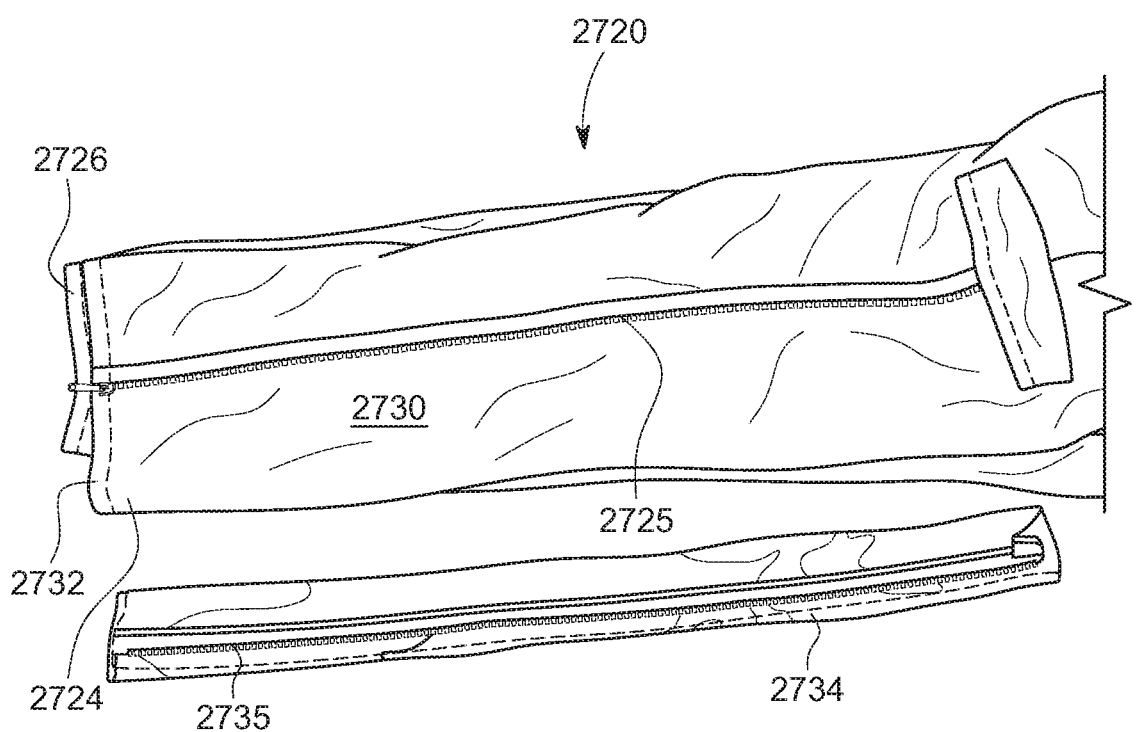
FIG. 28B shows a magnified view of the pants and the sensory strip shown in FIG. 28A.

Referring to FIGS. 28A and 28B, in one embodiment, pants 2720 have a waistband 2722 located at an upper end and first and second legs 2724, 2726 that extend down from the waistband 2722. In one embodiment, the first leg 2724 has an outside surface 2730 that extends from the waistband 2722 to the lower end 2732 of the first leg 2724. A first half 2725 of a zipper is secured to the outside surface 2730 of the first leg 2724. A sensory strip 2734 has structure for releasably attaching the sensory strip to the outside surface 2730 of the first leg 2724. In one embodiment, the first sensory strip 2734 has a second half 2735 of a zipper that is adapted to mesh with the first half 2725 of the zipper that is provided on the leg of the pants. The zipper is closed for releasably attaching the sensory strip to the leg. The zipper may be opened for detaching the sensory strip from the leg of the pants. Although FIGS. 28A and 28B show using a zipper for releasably securing the sensory strip 2734 to the pants leg 2724, other temporary attachment mechanisms may be used such as hook and loop fasteners, snaps, buttons, magnets, and laces.

Figure 29:
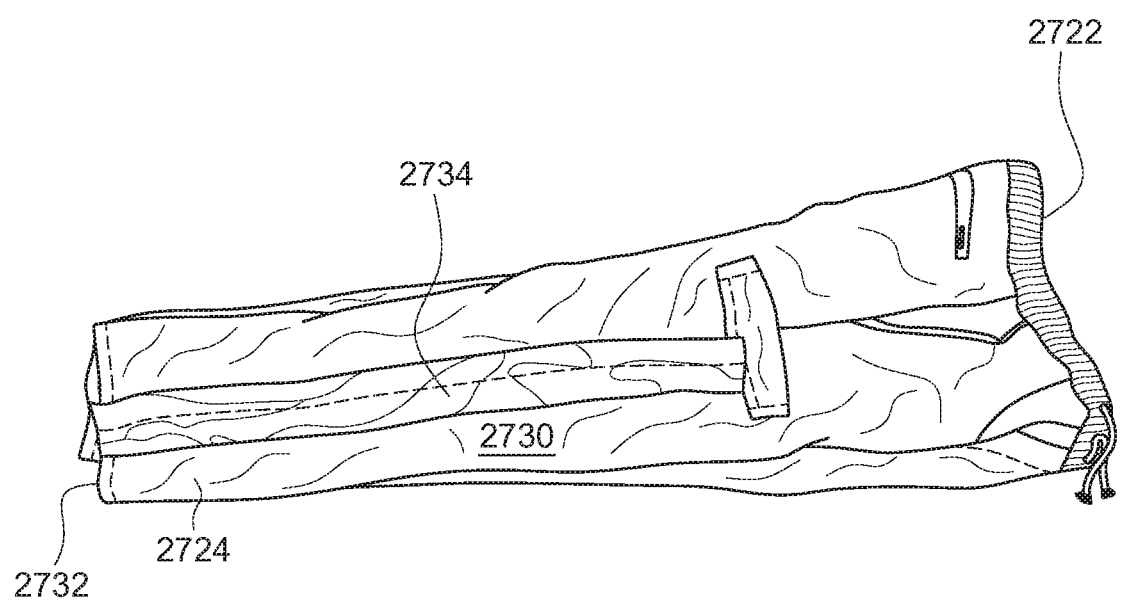
FIG. 29 shows the sensory strip of FIGS. 28A and 28B after being releasably attached to the leg of the pants.

FIG. 29 shows the sensory strip 2734 after it has been secured (e.g., zippered) to the outside surface 2730 of the first leg 2724 of the pants. Although FIG. 29 shows the sensory strip 2734 extending only part of the way between the lower end 2732 of the first leg 2724 and the waistband 2722, in other embodiments, the sensory strip 2734 may extend the entire distance between the lower end 2732 of the first leg 2724 and the waistband 2722, or any preferred distance therebetween.

Figure 30:
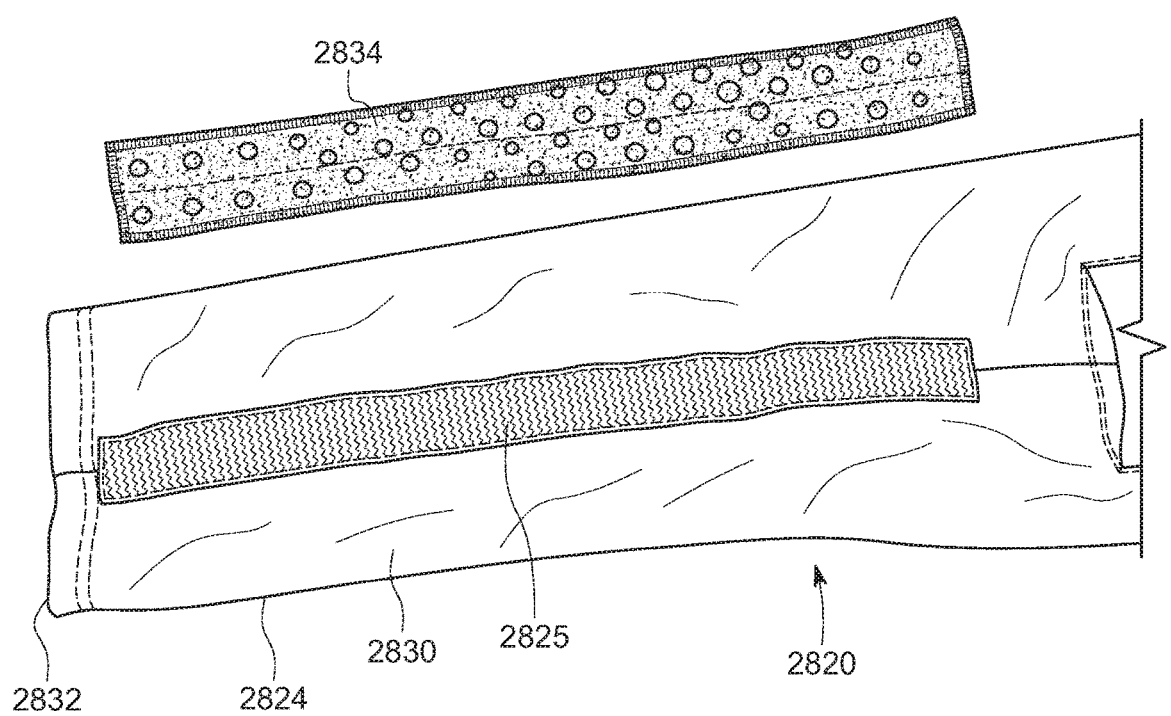
FIG. 30 shows pants and a top side of a sensory strip that is adapted to be releasably attached to a leg of the pants, in accordance with one embodiment of the present patent application.
Figure 31:
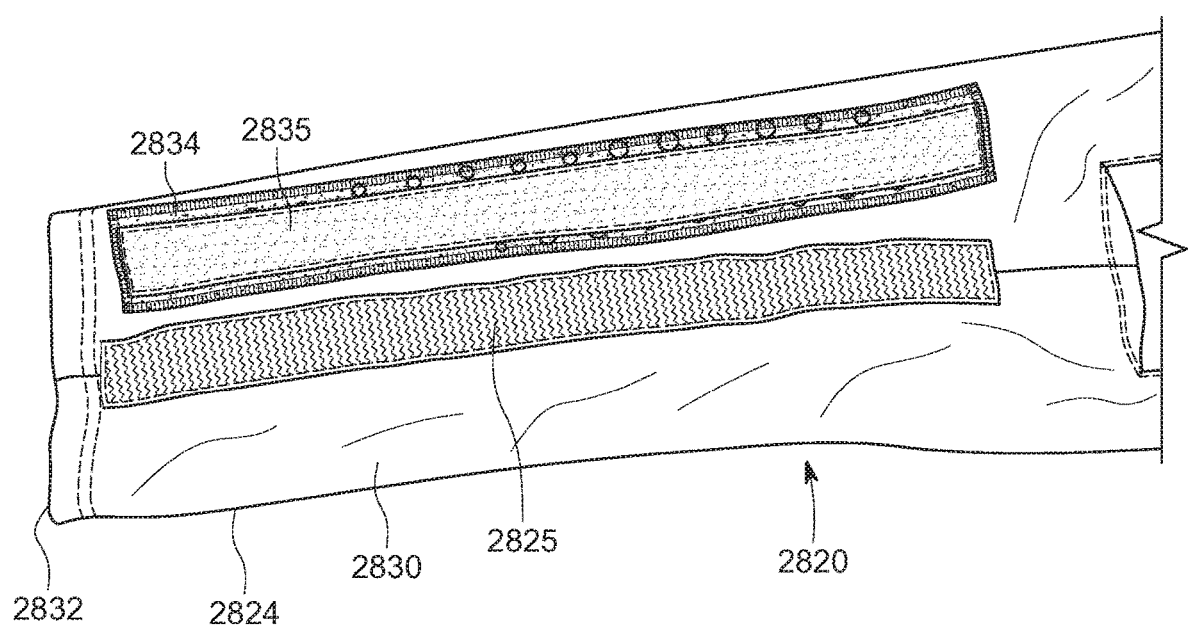
FIG. 31 shows a magnified view of the pants and an underside of the sensory strip shown in FIG. 30.

Referring to FIGS. 30 and 31, in one embodiment, pants 2820 have a waistband located at an upper end (not shown) and a first leg 2824, and a second leg (now shown) that extends down from the waistband. In one embodiment, the first leg 2824 has an outside surface 2830 that extends from the waistband to the lower end 2832 of the first leg 2824. A first half 2825 of a hook and loop fastener strip is secured to the outside surface 2830 of the first leg 2824. A sensory strip 2834 is adapted to be releasably attached to the outside surface 2830 of the first leg 2824. In one embodiment, the sensory strip 2834 has a second half 2835 of a hook and loop fastener strip that is adapted to mesh with the first half 2825 of the hook and loop fastener strip provided on the first leg of the pants. Although FIG. 30 shows using hook and loop fasteners for releasably securing the sensory strip 2834 to the first pants leg 2824, other temporary attachment mechanisms may be used such as zippers, snaps, buttons, magnets and laces.

Figure 32A:
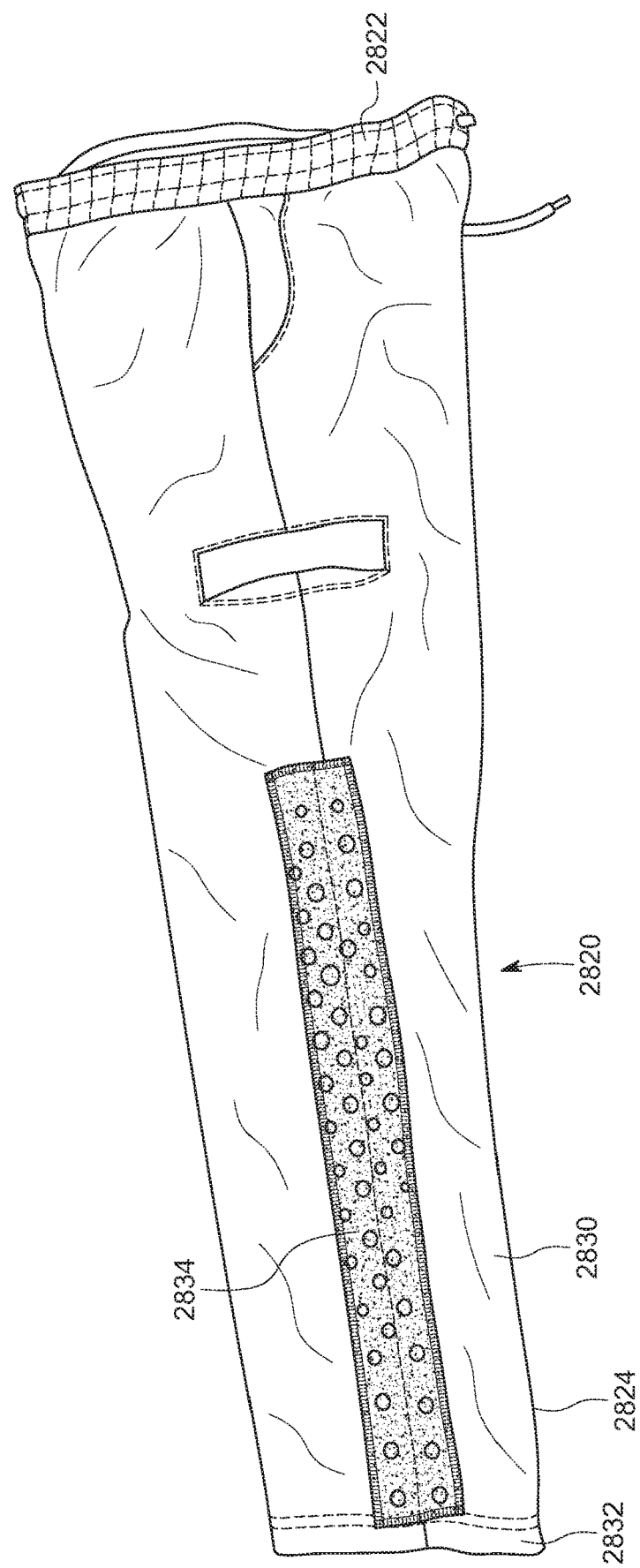
FIG. 32A shows the sensory strip of FIGS. 30 and 31 after the sensory strip has been releasably attached to the leg of the pants.

FIG. 32A shows the sensory strip 2834 after it has been releasably attached (e.g., velcroed) to the outside surface 2830 of the first leg 2824 of the pants 2820. Although FIG. 32A shows the sensory strip 2834 extending only part of the way between the lower end 2832 of the first leg 2824 and the waistband 2822, in other embodiments, the sensory strip 2834 may extend the entire distance between the lower end 2832 of the first leg 2824 and the waistband 2822, or any distance therebetween.

Figure 32B:
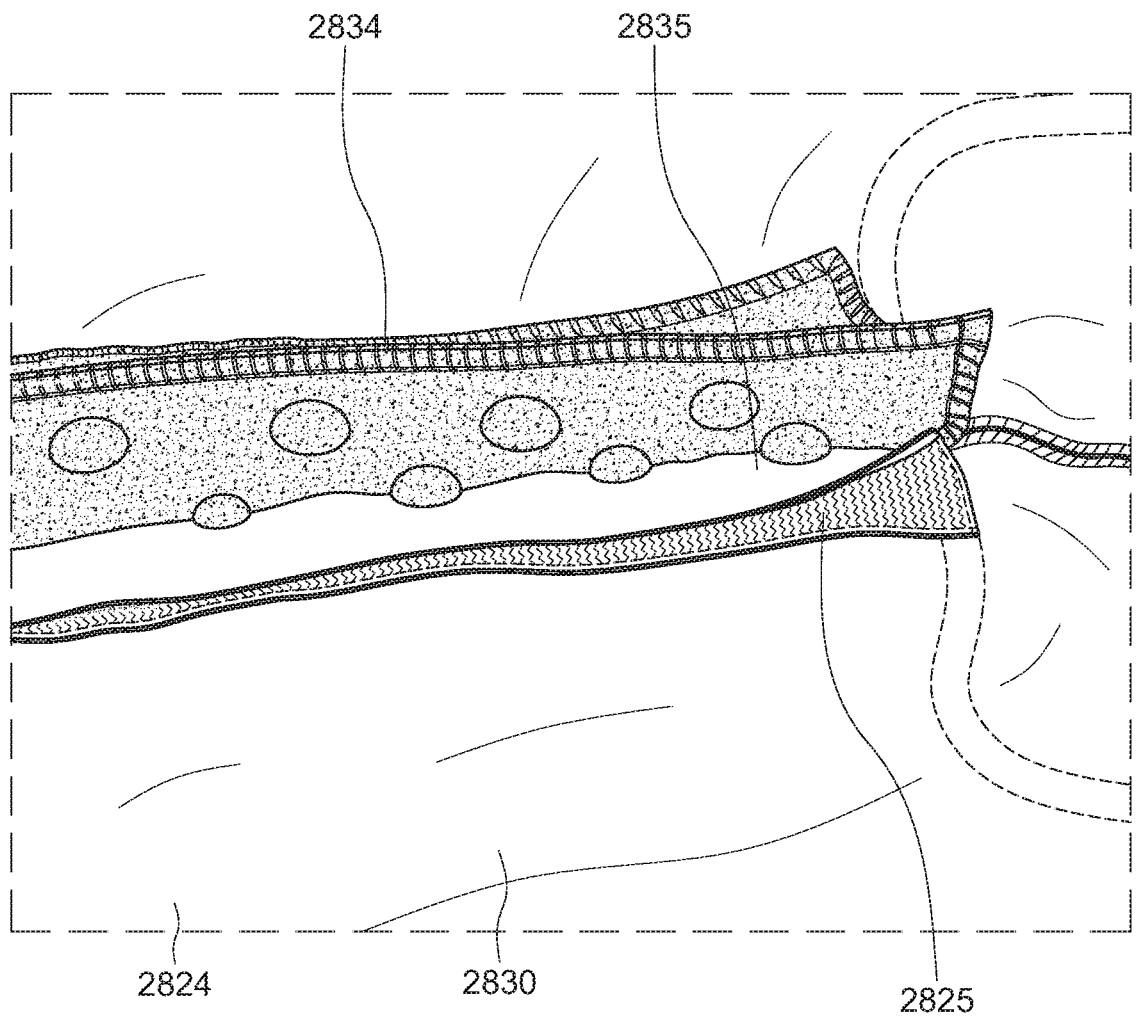
FIG. 32B shows a magnified view of the pants and the releasably attached sensory strip shown in FIG. 32A.

FIG. 32B shows a magnified view of the sensory strip 2834 with the first half 2825 of the hook and loop fastener strip on the outside surface 2830 of the first leg 2824 of the pants engaging with the second half 2835 of the hook and loop fastener strip exposed at an underside of the sensory strip. In one embodiment, the hook and loop fastener material releasably attaches the sensory strip 2834 to the outside surface 2830 of the first leg, which enables the sensory strip to be peeled away from the pants (i.e., detached) for attachment and use on another pair of pants or another clothing item.

In one embodiment, a kit may include two or more sensory strips having different properties such as different colors, patterns, holidays, sports, teams, subjects, themes, fabrics, textures, stitching, thicknesses, widths, accessories, etc. The purpose is to enable a user to mix and match sensory strips and clothing in an infinite number of different ways to allow the user to customize clothing and always wear a sensory strip that is desired by the user. Providing two or more sensory strips having different properties preferably enables users to customize clothing. For example, a first sensory strip having a first color for a favorite college football team may be releasably attached to clothing on a first day, and a second sensory strip having a second color for a favorite professional football team may be releasably attached to the clothing on a second day. The change may be made by detaching the first sensory strip from the clothing and then releasably attached the second sensory strip to the clothing.

In one embodiment, a user may remove a first sensory strip from a clothing item and then releasably attached a second sensory strip to the same clothing item. In one embodiment, the first and second sensory strips have different physical or structural features for providing a different sensation or different tactile feedback for a user.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. Therapeutic clothing comprising:
a garment including a waistband and first and second legs extending below said waistband;
a first sensory strip overlying an outside surface of said first leg and extending between said waistband and a lower end of said first leg, said first sensory strip having an inner edge and an outer edge;
a first fastening system for releasably attaching the inner edge of said first sensory strip over said outside surface of said first leg, wherein said first fastening system includes a first half secured to said outside surface of said first leg and a second half secured to the inner edge of said first sensory strip, wherein when the inner edge of said first sensory strip is releasably attached to said outside surface of said first leg, the outer edge of said first sensory strip comprises a flap of material that extends outwardly from said outside surface of said first leg for being engaged by an individual's fingers to provide sensory feedback;
a second sensory strip overlying an outside surface of said second leg and extending between said waistband and a lower end of said second leg, said second sensory strip having an inner edge and an outer edge;
a second fastening system for releasably attaching the inner edge of said second sensory strip over said outside surface of said second leg, wherein said second fastening system includes a first half secured to said outside surface of said second leg and a second half secured to the inner edge of said second sensory strip, wherein when the inner edge of said second sensory strip is releasably attached to said outside surface of said second leg, the outer edge of said second sensory strip comprises a flap of material that extends outwardly from said outside surface of said second leg for being engaged by the individual's fingers to provide sensory feedback;
wherein the outer edge of said first sensory strip comprises first cross-stitching that defines a first thicker section of said first sensory strip, and wherein the outer edge of said second sensory strip comprises second cross-stitching that defines a second thicker section of said second sensory strip.

2. The therapeutic clothing as claimed in claim 1, wherein the first and second halves of said first fastening system comprise hook and loop strips attached to said first sensory strip and said outside surface of said first leg, and wherein the first and second halves of said second fastening system comprise second hook and loop strips attached to said second sensory strip and said outside surface of said second leg.

3. The therapeutic clothing as claimed in claim 1, wherein the first half of said first fastening system comprises a first zipper half and the second half of said first fastening system comprises a second zipper half.

4. The therapeutic clothing as claimed in claim 3, wherein the first half of said second fastening system comprises a first zipper half and the second half of said second fastening system comprises a second zipper half.

5. The therapeutic clothing as claimed in claim 1, wherein said first fastening system comprises components selected from the group consisting of hook and loop fastener strips, zipper teeth, buttons, snaps, magnets and laces.

6. The therapeutic clothing as claimed in claim 1, wherein said first and second sensory strips are elongated, and wherein said first and second sensory strips have respective widths that project away from one another on opposite sides of said garment.

7. The therapeutic clothing as claimed in claim 1, wherein each of said first and second sensory strips has a length of 5-40 inches, a width of 0.5-3 inches, and a thickness of 0.0625-0.25 inches.

8. The therapeutic clothing as claimed in claim 1, wherein said first and second sensory strips comprise material selected from the group of materials consisting of cotton, cellulose, polymers, spandex, silicon, tweed, nylon, silk, satin, corduroy, polyester, rayon, velvet, nylon, cashmere, fur, and fake fur.

9. Therapeutic clothing comprising:
a garment adapted to be worn over a lower portion of a body comprising a waistband and first and second legs extending below said waistband;
a first elongated sensory strip overlying an outside surface of said first leg and extending along a length of said first leg between said waistband and a lower end of said first leg;
a first fastening system for releasably attaching said first elongated sensory strip to said outside surface of said first leg;
a second elongated sensory strip overlying an outside surface of said second leg and extending along a length of said second leg between said waistband and a lower end of said second leg; and
a second fastening system for releasably attaching said second elongated sensory strip to said outside surface of said second leg;
wherein said first elongated sensory strip comprises a first stiffening element embedded therein that extends along a length of said first sensory strip, and wherein said second elongated sensory strip comprises a second stiffening element embedded therein that extends along a length of said second sensory strip.

10. The therapeutic clothing as claimed in claim 9, wherein said first and second elongated sensory strips project away from one another on opposite sides of said garment, and have a length of 5-40 inches, a width of 1 inch, and a thickness of 0.0625-0.25 inches.

11. The therapeutic clothing as claimed in claim 9, wherein said first elongated sensory strip has a first free outer edge comprising first cross-stitching that defines a first thicker section of said first elongated sensory strip, and wherein said second elongated sensory strip has a second free outer edge comprising second cross-stitching that defines a second thicker section of said second elongated sensory strip.

12. The therapeutic clothing as claimed in claim 9, wherein said first and second elongated sensory strips comprise material selected from the group of materials consisting of cotton, cellulose, polymers, spandex, silicon, tweed, nylon, silk, satin, corduroy, polyester, rayon, velvet, nylon, cashmere, fur, fake fur, and fleece.

13. Therapeutic clothing comprising:
a garment including a waistband and first and second legs extending below said waistband;
a first sensory strip overlying an outside surface of said first leg and extending between said waistband and a lower end of said first leg;
a fastening system for releasably attaching said first sensory strip over said outside surface of said first leg, wherein said fastening system includes a first part provided on said first leg and a second part provided on said first sensory strip, wherein said first sensory strip comprises a first stiffening element embedded therein that extends along a length of said first sensory strip.

14. The therapeutic clothing as claimed in claim 13, further comprising:
   a second sensory strip overlying an outside surface of said second leg and extending between said waistband and a lower end of said second leg;
   a second fastening system for releasably attaching said second sensory strip over said outside surface of said second leg, wherein said second fastening system includes a first part provided on said outside surface of said second leg and a second part provided on said second sensory strip, wherein said second sensory strip comprises a second stiffening element embedded therein that extends along the length of said second sensory strip.

15. The therapeutic clothing as claimed in claim 14, wherein an outer edge of said first sensory strip comprises first zipper teeth that extend along a length of said first sensory strip, and wherein an outer edge of said second sensory strip comprises second zipper teeth that extend along a length of said second sensory strip.

\* \* \* \* \*